(12) United States Patent
Stokes et al.

(10) Patent No.: US 10,751,052 B2
(45) Date of Patent: Aug. 25, 2020

(54) SURGICAL DEVICE WITH OVERLOAD MECHANISM

(71) Applicant: Ethicon LLC, Guaynabo, PR (US)

(72) Inventors: Michael J. Stokes, Cincinnati, OH (US); Chester O. Baxter, III, Loveland, OH (US); David A. Deupree, Mason, OH (US); Gregory G. Scott, Cincinnati, OH (US); Disha V. Labhasetwar, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 260 days.

(21) Appl. No.: 15/674,096

(22) Filed: Aug. 10, 2017

(65) Prior Publication Data
US 2019/0046196 A1 Feb. 14, 2019

(51) Int. Cl.
| | | |
|---|---|---|
| *A61B 17/10* | (2006.01) | |
| *A61B 90/00* | (2016.01) | |
| *A61B 17/072* | (2006.01) | |
| *A61B 17/128* | (2006.01) | |
| *A61B 17/29* | (2006.01) | |
| *A61B 17/00* | (2006.01) | |

(52) U.S. Cl.
CPC ........ *A61B 17/10* (2013.01); *A61B 17/07207* (2013.01); *A61B 17/1285* (2013.01); *A61B 90/03* (2016.02); *A61B 2017/00367* (2013.01); *A61B 2017/2912* (2013.01); *A61B 2017/2919* (2013.01); *A61B 2090/032* (2016.02); *A61B 2090/034* (2016.02)

(58) Field of Classification Search
CPC combination set(s) only.
See application file for complete search history.

(56) References Cited

U.S. PATENT DOCUMENTS

| | | | | |
|---|---|---|---|---|
| 5,009,661 | A | * 4/1991 | Michelson | ......... A61B 17/1608 606/170 |
| 5,947,984 | A | * 9/1999 | Whipple | ........ A61B 17/320092 601/2 |
| 9,011,484 | B2 | 4/2015 | Reinauer et al. | |
| 2008/0083813 | A1 | * 4/2008 | Zemlok | .............. A61B 17/2909 227/181.1 |
| 2008/0255608 | A1 | 10/2008 | Hinman et al. | |
| 2011/0022052 | A1 | * 1/2011 | Jorgensen | .......... A61B 17/1611 606/83 |
| 2017/0172608 | A1 | 6/2017 | Madan et al. | |

FOREIGN PATENT DOCUMENTS

| | | |
|---|---|---|
| EP | 1908426 A1 | 4/2008 |
| WO | 2016/057281 A1 | 4/2016 |

* cited by examiner

*Primary Examiner* — Tuan V Nguyen
(74) *Attorney, Agent, or Firm* — Mintz Levin Cohn Ferris Glovsky and Popeo, P.C.

(57) ABSTRACT

Surgical devices and methods for operating surgical devices during a surgical procedure are provided. In one exemplary embodiment, a surgical device is provided having a handle housing with an elongate shaft, an end effector on the distal end of the elongate shaft, a drive assembly, and a trigger coupled to the handle housing. Various overload mechanisms are provided for transferring a closing force from the trigger to the drive assembly unless the closing force exceeds a predetermined threshold force in which case the overload mechanism prevents transfer of the closing force to the drive assembly.

15 Claims, 23 Drawing Sheets

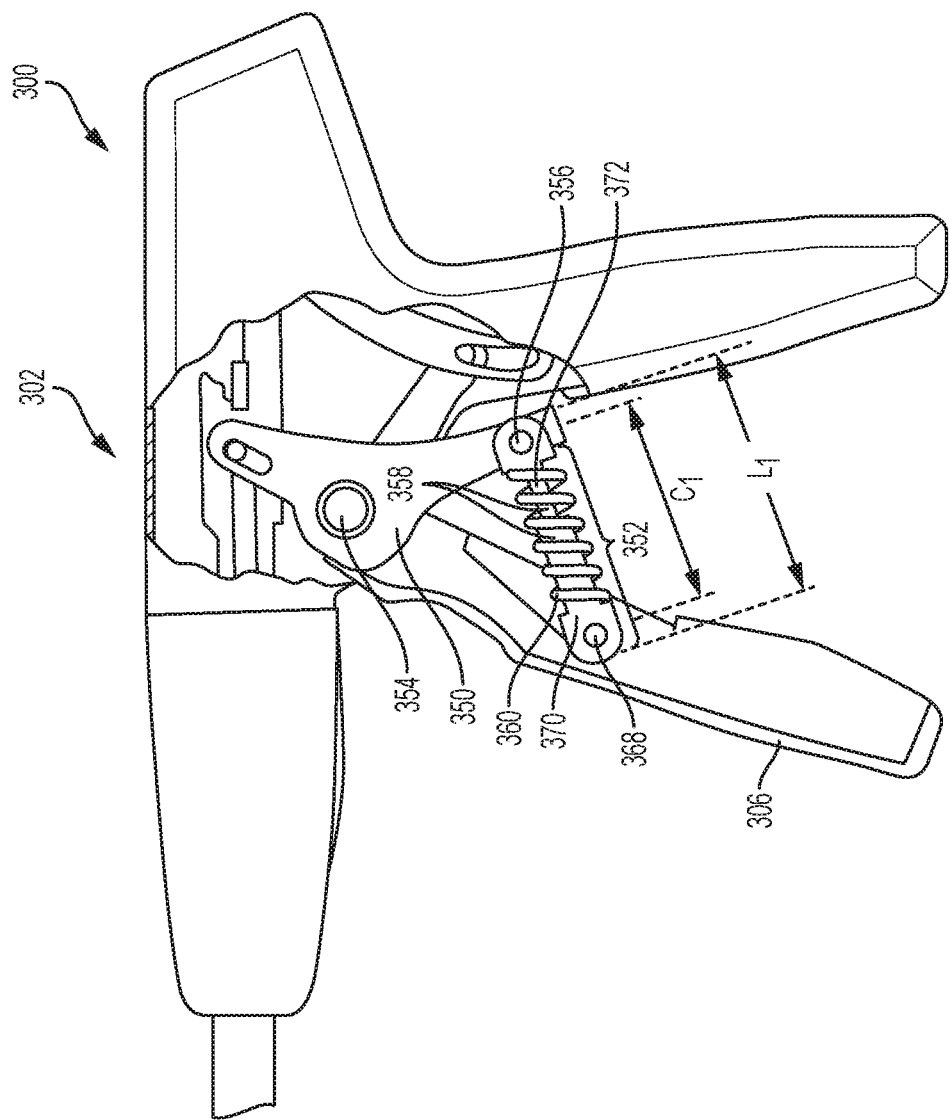

SURGICAL DEVICE WITH OVERLOAD MECHANISM

FIELD

Surgical devices and methods for using the same are provided.

BACKGROUND

Many laparoscopic devices include a pair of jaws for grasping, stapling, or otherwise effecting tissue. For example, surgical clip appliers are commonly used for ligating a blood vessel, a duct, shunt, or a portion of body tissue during surgery. Most clip appliers typically have a handle with an elongate shaft having a pair of movable opposed jaws formed on an end thereof for holding and forming a ligation clip therebetween. The jaws are positioned around the vessel or duct in, and the clip is crushed or formed on the vessel by the closing of the jaws.

Movement of the jaws between open and closed positions is controlled by a former assembly, which transmits a force from the handle to the opposed jaws. The force required to close the jaws can increase with thicker or stiffer tissue, and/or in applications where the jaws are applying a closure mechanism, such as a clip or staple, to the tissue. In the event that excessive forces are transmitted by the former assembly, undesired damage to the tissue can result. In addition, since the former assembly requires precise timing and coordinated movement between numerous other components, excessive forces applied to close the jaws can result in damage to the jaws, the former assembly, or additional components of the surgical clip applier.

Accordingly, despite existing technologies, there remains a need for improved devices and methods for preventing overload of a force applied to close opposed jaws of a surgical device.

SUMMARY

Surgical devices and methods for using the same are provided herein. In one exemplary embodiment, a surgical device is provided and can include a handle housing having an elongate shaft extending distally therefrom with an end effector at the distal end of the elongate shaft. The surgical device can also include a drive assembly configured to actuate the end effector, and a trigger coupled to the handle housing and pivotable about a trigger pivot axis from an unactuated position to an actuated position. A pivot linkage can be provided with a first end coupled to a drive assembly and a second end. The pivot linkage can be pivotable about the trigger pivot axis. The device can further include an overload member coupled at least between the second end of the pivot linkage and the trigger. Pivotal movement of the trigger about the trigger pivot axis from the unactuated position to the actuated position can transfer a closing force through the overload member to the second end of the pivot linkage thereby causing the pivot linkage to pivot about the trigger pivot axis such that the first end of the pivot linkage distally advances the drive assembly to cause actuation of the end effector. When the closing force exceeds a predetermined threshold force, pivotal movement of the trigger about the trigger pivot axis from the unactuated position to the actuated position can transfer the closing force to the overload member to cause the overload member to move in a manner that prevents transfer of the closing force to the pivot linkage such that the pivot linkage remains stationary relative to the handle housing.

The overload member can have a variety of configurations. In one embodiment, the overload member can include an overload linkage and a biasing element. The biasing element can bias the overload linkage to a first position when the trigger pivots about the trigger pivot axis from the unactuated position to the actuated position until the closing force exceeds the predetermined threshold force. In one aspect, when the closing force exceeds the predetermined threshold force, the closing force can overcome a biasing force of the biasing element to allow the overload member to move from the first position to a second position, thereby preventing further movement of the pivot linkage relative to the handle housing. In another aspect, when the closing force exceeds the predetermined threshold force, the biasing element can compress to thereby cause at least one of deflection of the overload member and reduction of a length of the overload member.

In another aspect, the overload linkage can have first and second ends in which the second end of the overload linkage can be slidably disposed within the trigger. For example, the biasing element can be housed within the trigger and, when the closing force exceeds the predetermined threshold force, the second end of the overload linkage can slide within the trigger to compress the biasing element such that the pivotal linkage remains stationary relative to the handle housing.

In other aspects, the biasing element can be positioned about an outer surface of the overload linkage such that, when the closing force exceeds the predetermined threshold force, the biasing element can compress to prevent further movement of the pivot linkage relative to the handle housing. In one embodiment, the compression of the biasing element can decrease a length of the overload member.

In another aspect, the pivot linkage can include a first portion and a second portion and the biasing element can be a deflectable region of the second portion of the pivot member such that, when the closing force exceeds the predetermined threshold force, the biasing element can deform to prevent further movement of the pivot linkage relative to the handle housing. In one embodiment, the first portion can be less flexible than the second portion of the pivot linkage.

In another embodiment, a surgical device is provided and can include a handle housing having a trigger pivotally coupled thereto, an elongate shaft extending distally from the handle housing with an end effector at a distal end thereof, a drive assembly movable to actuate the end effector, and a linkage assembly coupled between the trigger and the drive assembly. The linkage assembly can include a pivot member and an overload shaft coupled to one another. The pivot member can be coupled to the drive assembly and the overload shaft can be coupled to the trigger. The linkage assembly can be configured to transfer a driving force from the trigger, through the overload shaft to the pivot member to move the drive assembly and thereby actuate the end effector. The linkage can also be configured to cause the overload shaft to move while the pivot member remains stationary relative to the handle housing when the driving force exceeds a predetermined threshold force.

In one embodiment, the overload shaft can be operably connected to a biasing element that biases the overload shaft to a first position until the driving force exceeds the predetermined threshold force. In one aspect, when the driving force exceeds the predetermined threshold force, the driving force can cause the biasing element to move to allow the overload shaft to move from a first position to a second position, thereby preventing further movement of the pivot member relative to the handle housing. In another aspect, the biasing element can be disposed within the trigger and the biasing element can have a first end that contacts an end of the overload shaft and a second end. In other aspects, the biasing element can be positioned about an outer surface of the overload shaft. In yet other aspects, the pivot member can have a proximal portion that is coupled to the drive assembly and a distal portion that is coupled to the overload shaft. The biasing element can be a deflectable region of the distal portion of the of the pivot member. In one embodiment, the proximal portion of the pivot member can be less flexible than the distal portion of the pivot member.

Methods for operating a surgical device are also provided. In one embodiment, the method can include manipulating an end effector on a distal end of an elongate shaft of a surgical device to position the end effector about tissue. The method can also include actuating a trigger on the surgical device to transfer a force from the trigger through an overload member to a pivot member to actuate a drive assembly that moves the end effector. The overload member can move relative to the handle housing when the force exceeds a predetermined threshold force to thereby prevent the force from being transferred to at least a portion of the pivot member.

In one embodiment, when the force exceeds the predetermined threshold, the overload member can move to prevent the force from being transferred to the pivot member. In another embodiment, the overload member can include an overload linkage coupled to a deflectable region of the pivot member, and when the force exceeds the predetermined threshold force, the overload linkage can move thereby deforming the pivot member at the deflectable region.

BRIEF DESCRIPTION OF THE DRAWINGS

This invention will be more fully understood from the following detailed description taken in conjunction with the accompanying drawings, in which:

FIG. 7A is a perspective, partially transparent view of a proximal portion of a surgical clip applier having an overload member that includes a biasing element disposed within an overload linkage, showing the trigger and the overload member in unactuated positions;

DETAILED DESCRIPTION

Figure 1:
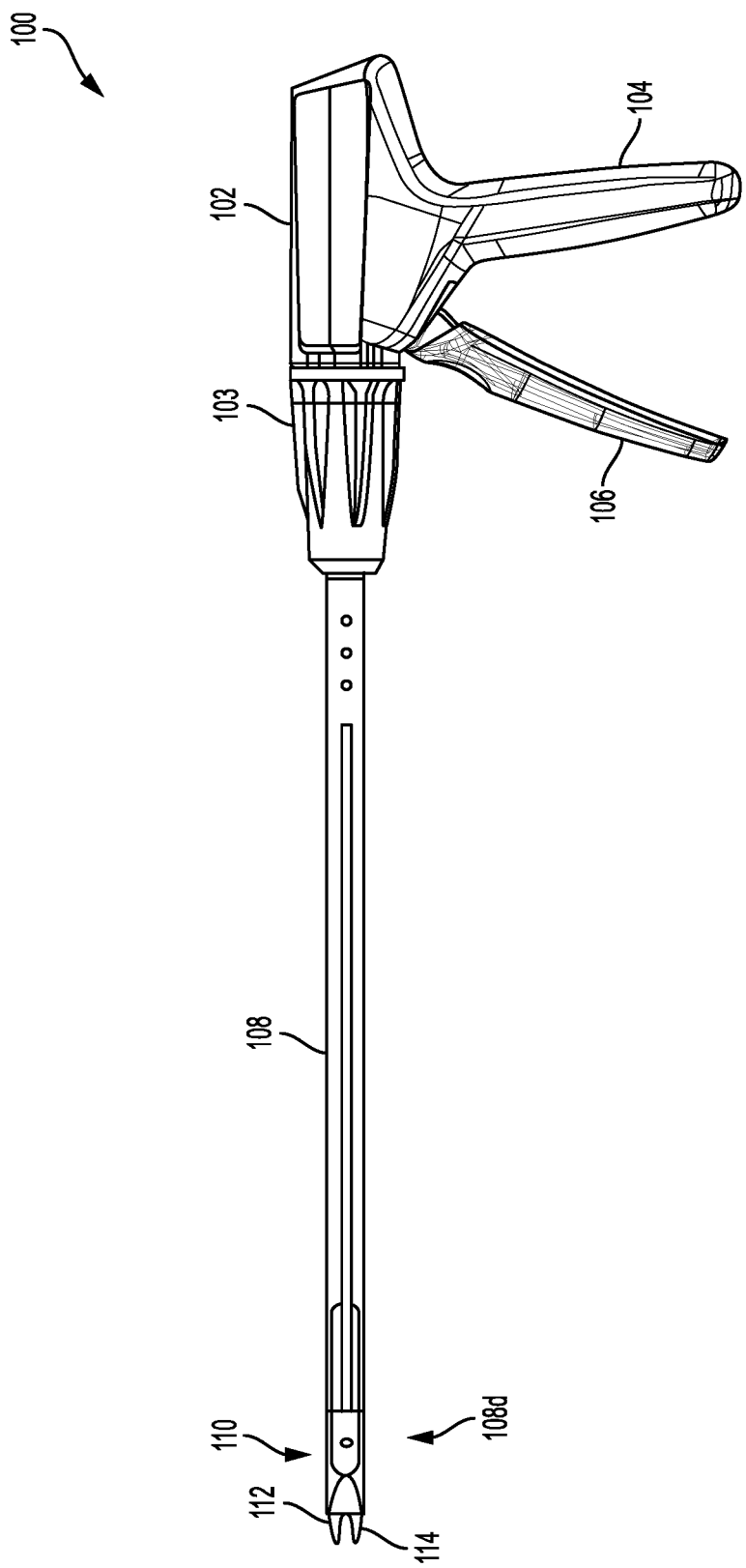
FIG. 1 is a side view of one exemplary embodiment of a conventional surgical clip applier.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Surgical devices and methods are provided for preventing an overload force from transferring to an end-effector on the surgical device when the force exceeds a predetermined threshold force. In general, a surgical device is provided having a handle housing and an elongate shaft extending distally therefrom with an end effector coupled to a distal end. A trigger is coupled to the handle housing and movable between an unactuated position and an actuated position for causing corresponding movement of the end effector. The device can further include an overload mechanism that prevents an excessive closure force from being applied to the end effector when resistance is encountered. For example, when the surgical device is a surgical clip applier, the overload mechanism can allow the trigger to continue to move toward the actuated position without causing further closing of the opposed jaws. An exemplary surgical clip applier can include a variety of features to facilitate application of a surgical clip, as described herein and illustrated in the drawings. However, a person skilled in the art will appreciate that the surgical clip applier can include only some of these features and/or it can include a variety of other features known in the art. The surgical clip appliers described herein are merely intended to represent certain exemplary embodiments. Moreover, while the overload mechanisms are described in connection with surgical clip appliers, the overload mechanisms can be used in connection with any type of surgical device.

FIGS. 1-4B illustrate one embodiment of a conventional surgical clip applier 100. As shown, the surgical clip applier 100 generally includes a housing 102 having a stationary handle 104 and a movable handle or trigger 106 that is pivotally coupled to the housing 102. An elongate shaft 108 extends distally from the housing 102 and includes a jaw assembly 110 formed on a distal end 108d thereof and including first and second jaws 112, 114 that are movable between open and closed positions. The first and second jaws 112, 114 include opposed inward facing surfaces and each inward facing surface has a clip track formed therealong for receiving and guiding legs of a clip into the first and second jaws 112, 114. The elongate shaft 108 can be rotated with respect to the housing 102 via a rotation knob 103.

Figure 2:
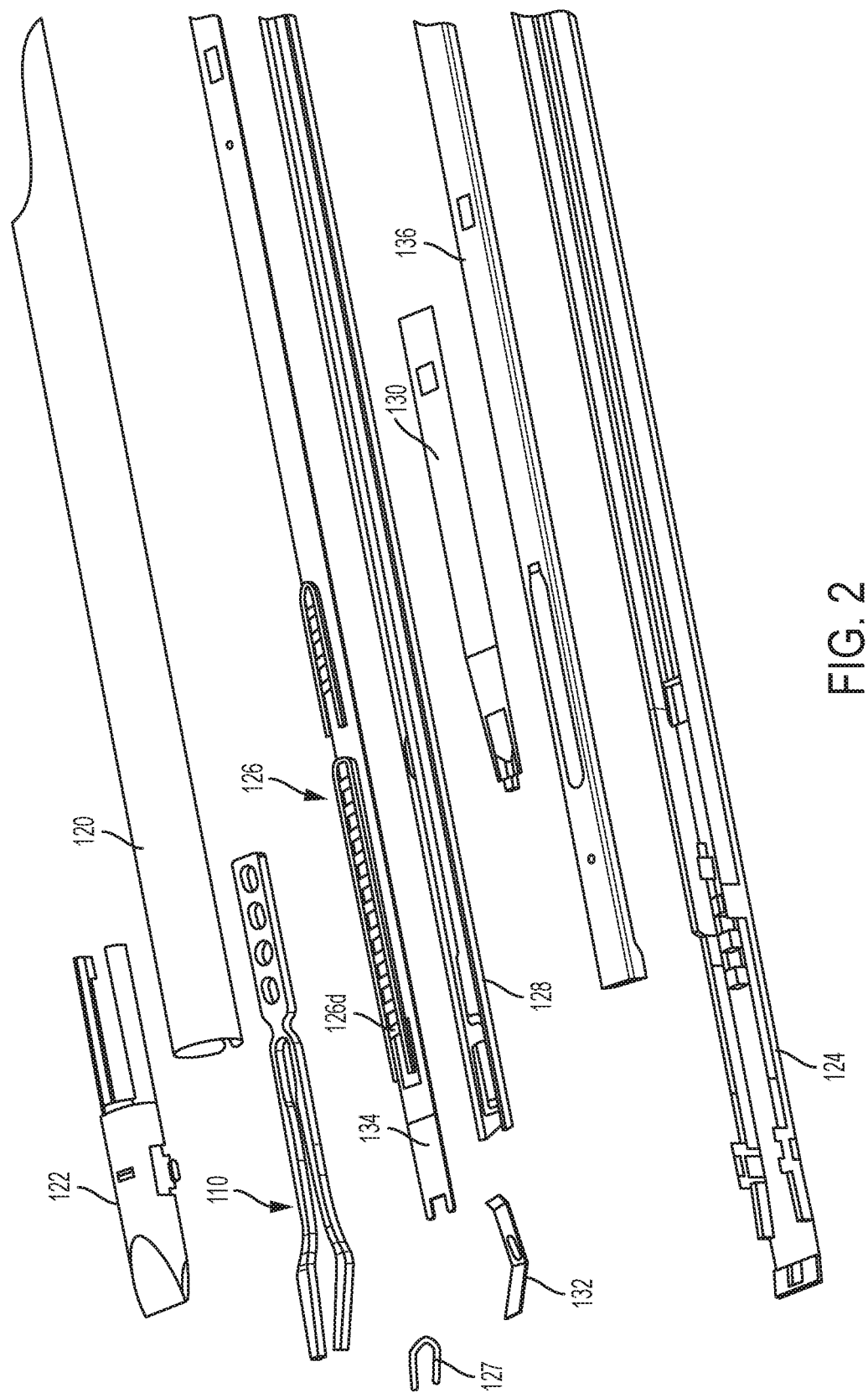
FIG. 2 is an exploded view of a distal portion of the surgical clip applier of FIG. 1.
Figure 3:
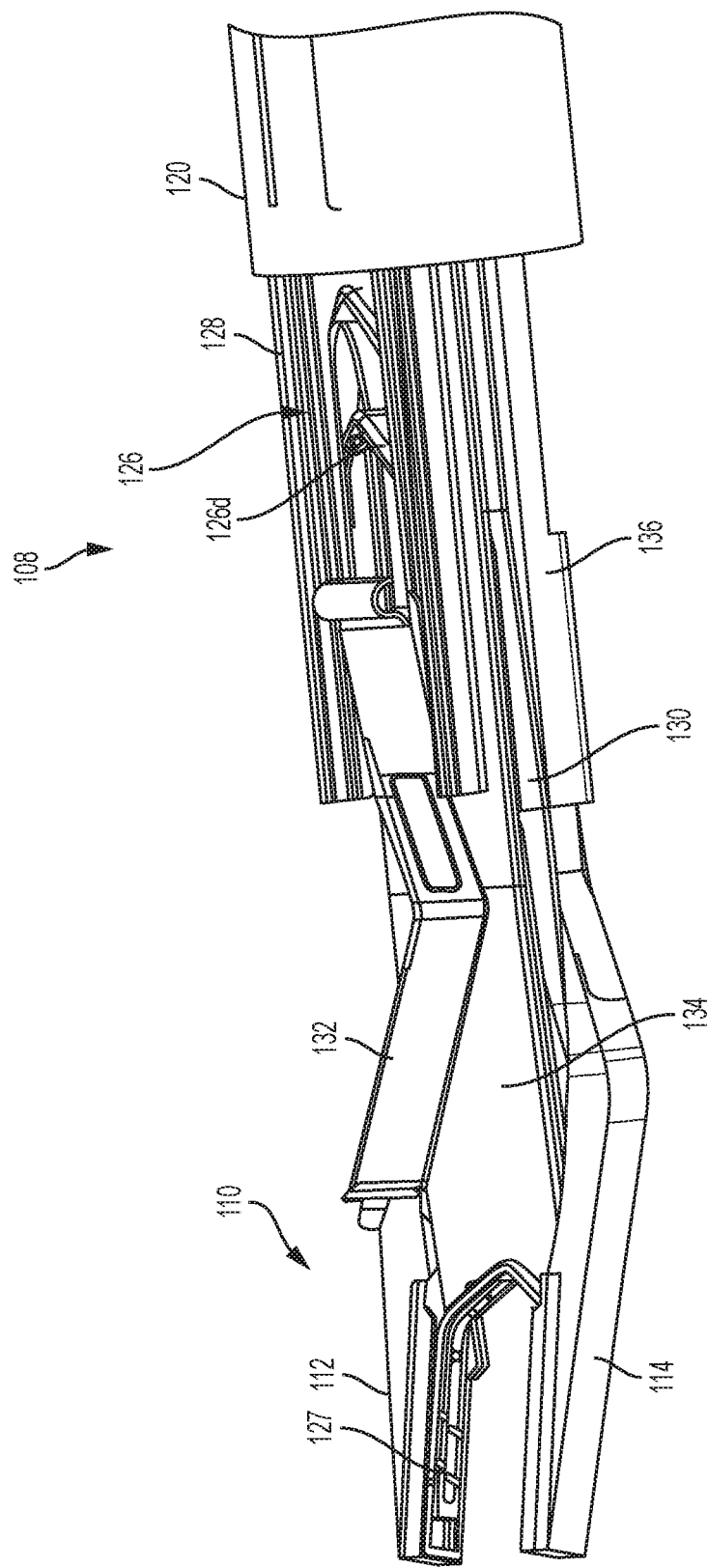
FIG. 3 is a perspective view of a distal portion of the surgical clip applier of FIG. 1.

As shown in FIGS. 2 and 3, the elongate shaft 108 can include an outer support tube 120, an upper shroud 122 coupled distally to the outer support tube 120, and a lower shroud 124. The outer support tube 120 and the upper and lower shrouds 122, 124 form an outer casing of the shaft 108. As shown in FIGS. 2 and 3, a clip stack 126 including multiple surgical clips is disposed within a clip track or holder 128 of the shaft 108 proximal to the first and second jaws 112, 114, and is biased distally. A floor 130 extends beneath the clip stack 126 for maintaining the clip stack 126 in alignment within the shaft 108, and for guiding a distal-most clip 126d into the jaws 112, 114. A lifter spring 132 is positioned just proximal to the jaws 112, 114 and distal to the clip stack 126 for preventing distal movement of the clip stack 126, with the distal-most clip 126d disposed around the lifter spring 132. A feeder bar 134 extends through the elongate shaft 108 for feeding the distal-most clip 126d into the jaws. As shown in FIG. 3 illustrating the clip applier 100 with the upper and lower shrouds 122, 124 removed, a former tube 136 extends around a proximal end of the jaws 112, 114 and is movable distally to cam the jaws 112, 114 to a closed position for forming a clip 127 disposed therebetween.

Figure 4A:
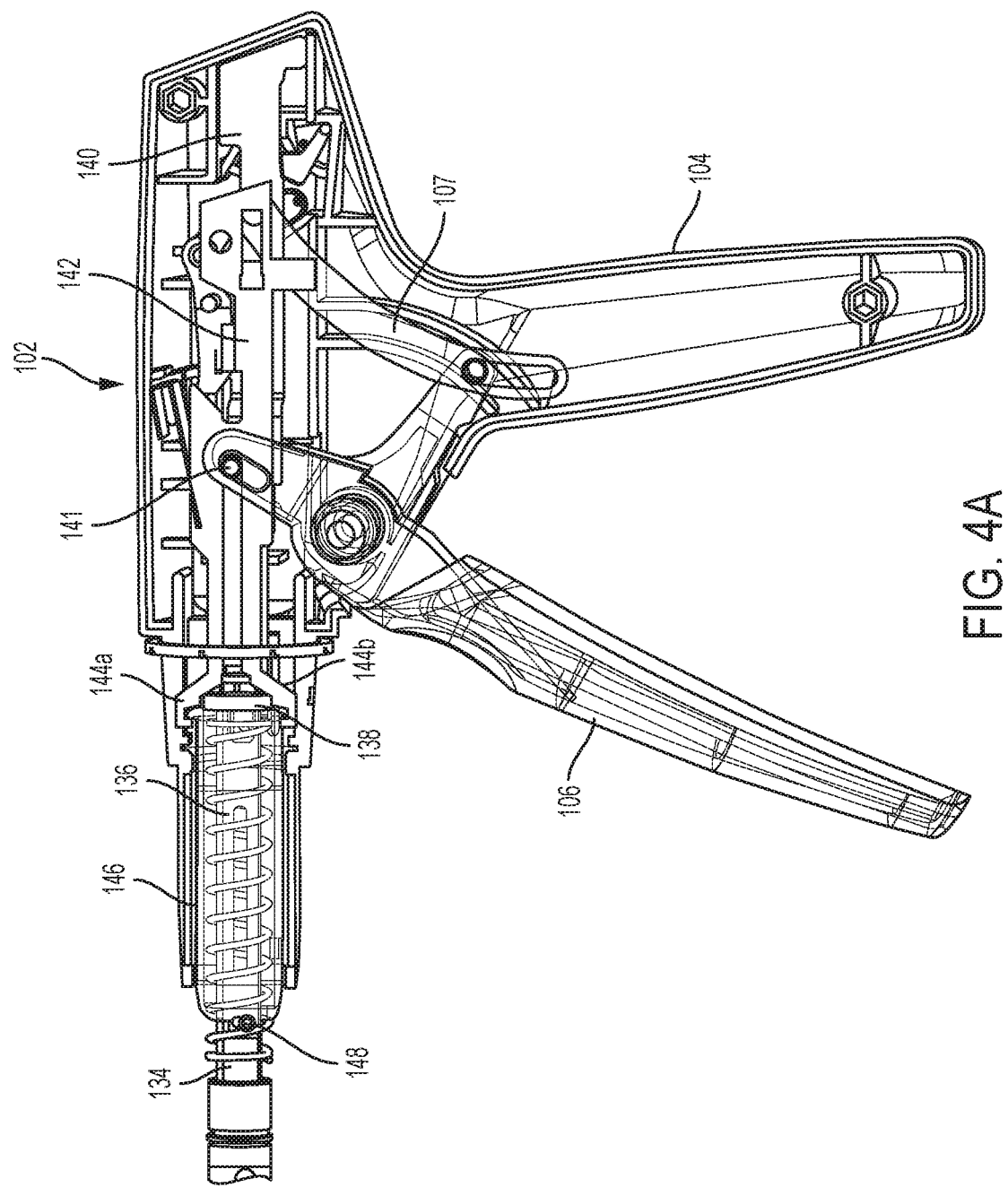
FIG. 4A is a perspective, partially transparent view of a proximal portion of the surgical clip applier of FIG. 1.
Figure 4B:
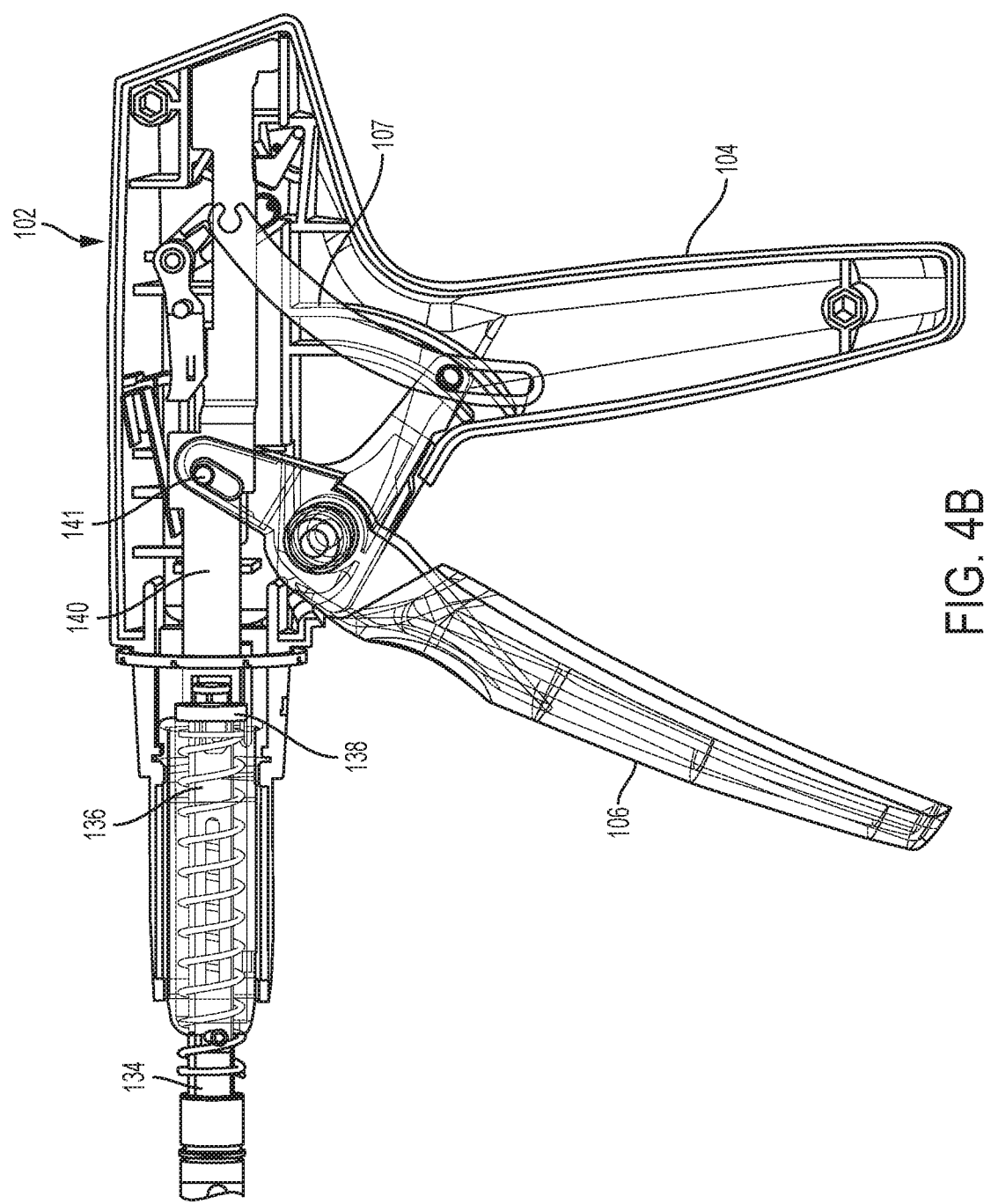
FIG. 4B is another perspective, partially transparent view of the proximal portion of the surgical clip applier of FIG. 1.

The surgical clip applier 100 has a clip forming assembly including various components that operate together to close the jaws 112, 114 when the trigger 106 is activated to thereby cause a clip (e.g., clip 127) disposed in the jaws to be applied (formed) to the tissue. The clip forming assembly encompasses the former tube 136 and other components that are coupled to the trigger 106 configured to be activated to move the former tube 136 distally to thereby close the jaws 112, 114. A clip advancing assembly of the surgical clip applier 100 includes the feeder bar 134 that is also coupled to the trigger 106, via a link 107 extending proximally from the trigger 106, as shown in FIGS. 4A and 4B. In this way, when the trigger 106 is activated, the feeder bar 134 is caused to move proximally, opposite to a distal direction in which the former tube 136 is moved upon activation of the trigger 106.

The clip forming and clip advancing assemblies can have any suitable configurations. For example, in the illustrated embodiment, as shown in FIGS. 4A and 4B, the former tube 136 of the clip forming assembly is coupled, via an inner coupling 138, to a former plate 140 in the housing 102 that is, in turn, coupled to the trigger 106 via a pin 141, and the feeder bar 134 of the clip advancing assembly is coupled to the trigger 106 via a feeder plate 142 that is also coupled to the trigger 106, via the link 107. As shown in FIG. 4A, the feeder plate 142 has arms 144a, 144b at a distal end thereof that are disposed over and mate with a proximal end of an outer coupling 146 (shown partially transparent). A connecting pin 148 at a distal end of the outer coupling 146 attaches the feeder bar 134 to the outer coupling 146. FIGS. 4A and 4B illustrate the housing 102 with part of an outer casing removed, and FIG. 4B shows the housing 102 without the feeder plate 142, for illustration purposes only. It should be appreciated that the surgical clip applier 100 can include various other components and assemblies that are not described herein for the sake of simplicity.

In use, when the trigger 106 of the housing 102 is activated (e.g., moved towards the stationary handle 104), the former plate 140 of the clip forming assembly is advanced distally to cause the former tube 136 to advance distally over the jaws 112, 114, thereby camming the jaws 112, 114 to the closed position. At the same time, the feeder plate 142 of the clip advancing assembly is moved proximally, thereby pulling the feeder bar 134 proximally to position the feeder bar 134 proximal of the distal-most clip 126d of the clip stack 126. Once the clip 127, disposed in the jaws 112, 114 such that clip's legs are received within the clip track of each of the jaws, is fully formed, the trigger 106 is released, which causes the clip forming assembly to move proximally while the clip advancing assembly moves distally. FIG. 2 shows the clip 127 in an original, pre-formed configuration. The proximal movement of the clip forming assembly causes the former tube 136 to retract relative to the jaws, thus allowing the jaws 112, 114 to move to the original open position, thereby releasing the formed clip. The distal movement of the clip advancing assembly causes the feeder bar 134 to move distally, and the feeder bar 134 thereby pushes the distal-most clip 126d distally, overcoming the biasing force of the lifter spring 132 and causing the lifter spring 132 to deflect out of the way, thereby allowing the distal-most clip 126d to be advanced into the jaws 112, 114. In this way, the distal-most clip becomes positioned in the jaws' clip tracks, like the clip 127 in FIG. 3. The floor 130 helps guide the distal-most clip into the clip tracks of the jaws 112, 114.

A person skilled in the art will appreciate that, while overload mechanisms are shown and described below, the overload mechanisms disclosed herein can be coupled to other actuation mechanisms, and need not be coupled to a trigger as described. For example, the clip applier can be powered and the overload mechanism can be coupled to an actuation button for actuating a motor to control firing of the device. In other embodiments, the overload mechanism can be configured to couple to a robotic system, such that actuation of the device is controlled through the robotic system.

As discussed above, a closing force is applied to move the trigger 106 from an unactuated position to an actuated position, thereby advancing a distal-most clip 126d into the jaws 112, 114. As the clip forming process proceeds and the clip 127, now disposed in the jaws 112, 114, is at least partially deformed about the tissue, the closing force required to continue closing the jaws 112, 114 around the clip 127 can significantly increase when, for example, the clip 127 is formed about thick and/or incompressible tissue, formed about a previous formed clip about the tissue of interest, and/or formed about other hard objects located about the tissue of interest.

An increase in the closing force can result in overload on the jaws 112, 114. For example, during the closing stroke of the trigger 106, a reaction force from the former tube 136 can be encountered. When this occurs, a user typically applies excessive closing force to the trigger 106 to overcome this reaction force and to complete the closing stroke (i.e., moving the trigger 106 to the actuated position). This can cause the former tube 136 to unduly force the jaws 112, 114 closed, which can result in deformation of the jaws 112, 114 and/or damage to other components of the surgical clip applier 100. This deformation of the jaws 112, 114 can cause improper formation of formed clips and/or premature release of preformed or partially formed clips and/or damage to tissue positioned between the jaws 112, 114.

Accordingly, various embodiments of an overload mechanism are provided for limiting a maximum force applied to the jaw assembly 110 of the surgical clip applier 100 to avoid overload on the jaws 112, 114. In general, the overload mechanisms provided herein are designed and positioned between the trigger 106 (or other actuation mechanisms) and the clip forming assembly such that when the closing force exceeds a predetermined threshold, the closing force is transferred to the overload mechanism instead of the clip forming assembly, thereby preventing the jaws 112, 114 from being improperly forced closed. Furthermore, these overload mechanisms can be designed having a similar path of movement of a conventional trigger, and therefore incorporation of the overload mechanisms described herein into conventional surgical clip appliers, like surgical clip applier 100 in FIGS. 1-4B, would not necessarily require changes, let alone substantial changes, to other internal mechanisms of the surgical clip appliers.

Figure 5A:
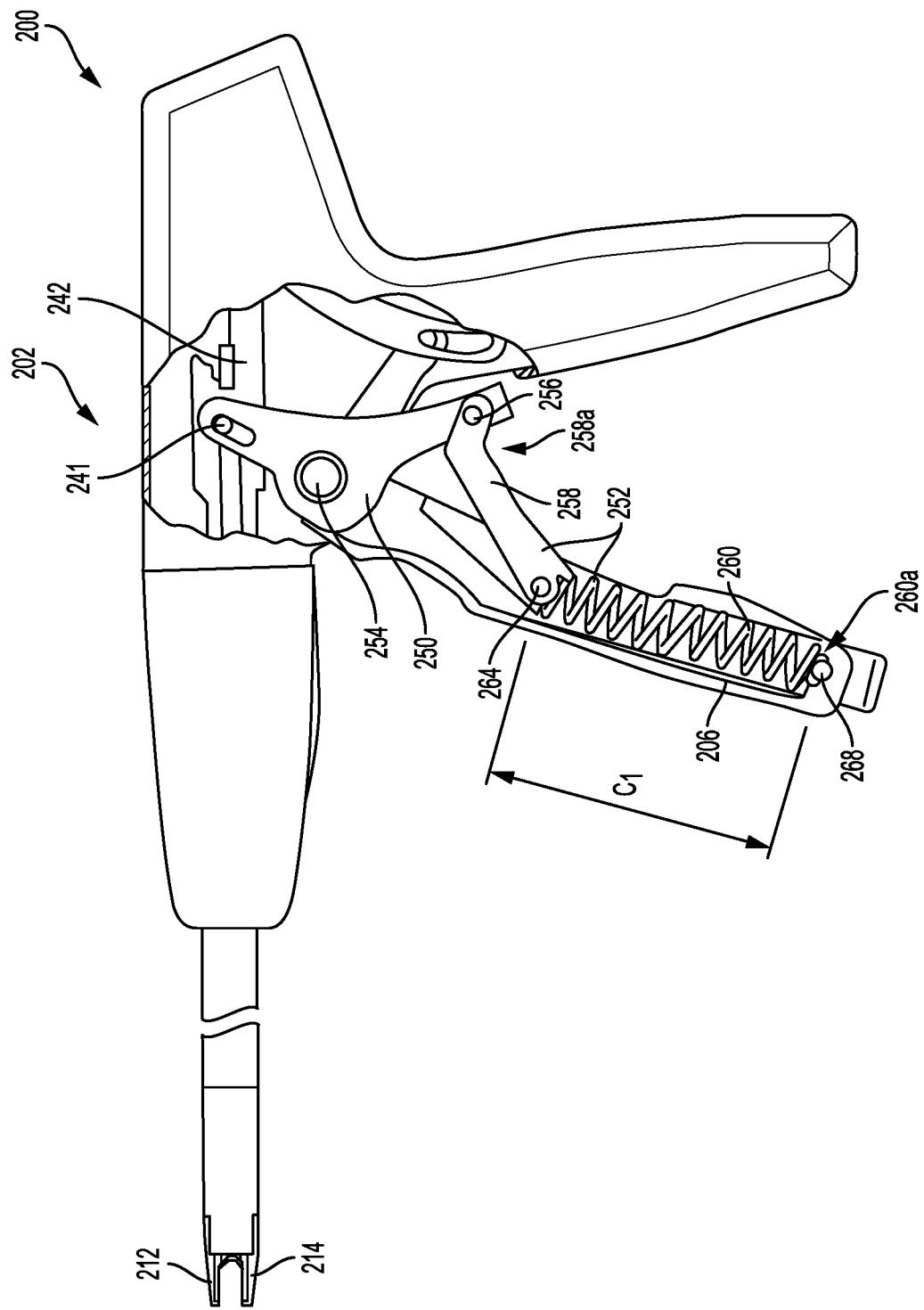
FIG. 5A is a perspective, partially transparent view of a surgical clip applier having an overload member that includes a biasing element housed within the trigger and an overload linkage operatively coupling the biasing element to a pivot linkage, showing the trigger and the overload member in unactuated positions.
Figure 5B:
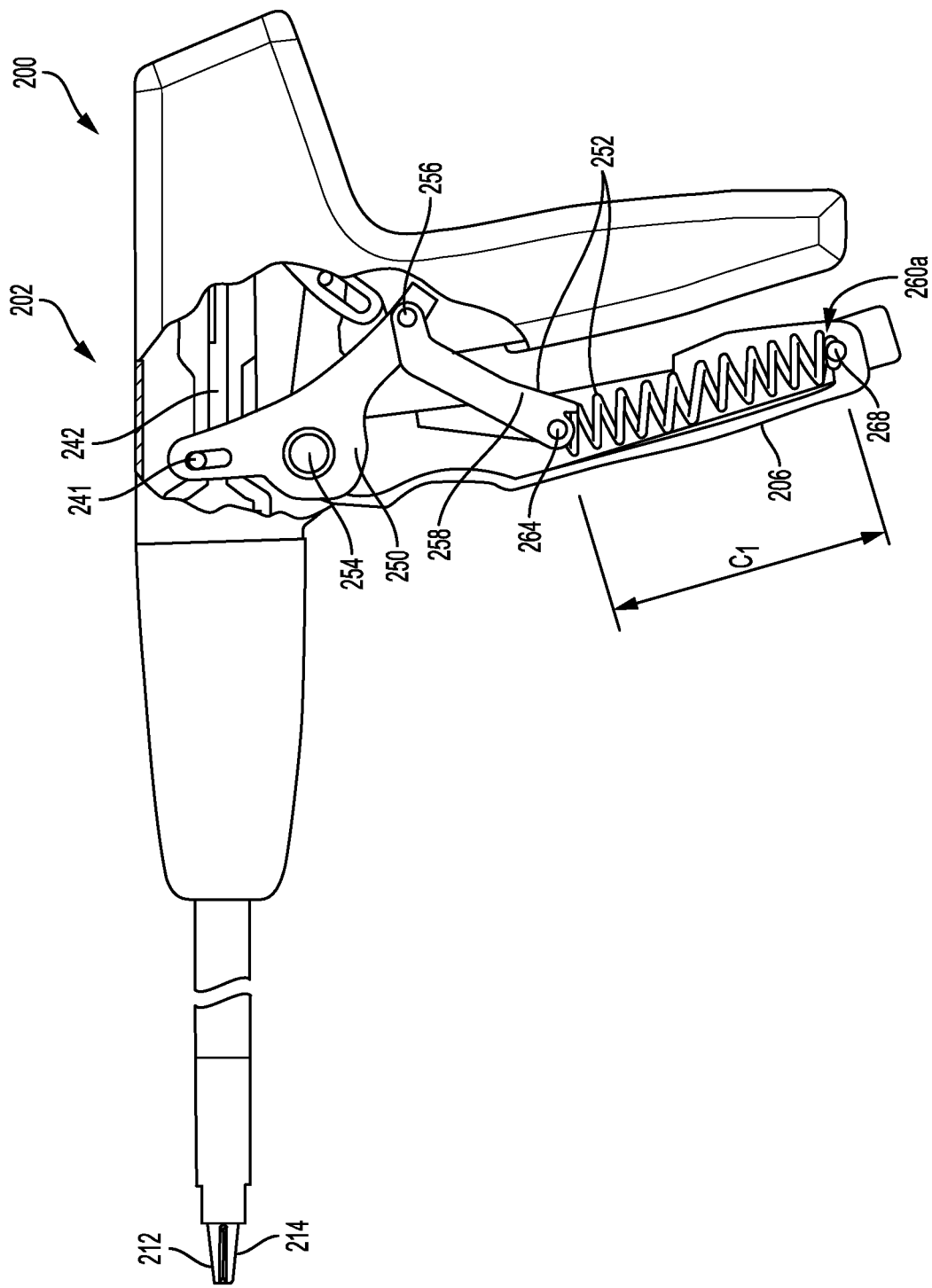
FIG. 5B is a perspective, partially transparent view of the surgical clip applier in FIG. 5A, showing the trigger in an actuated position and the overload member in a first position without the biasing element being compressed.
Figure 5C:
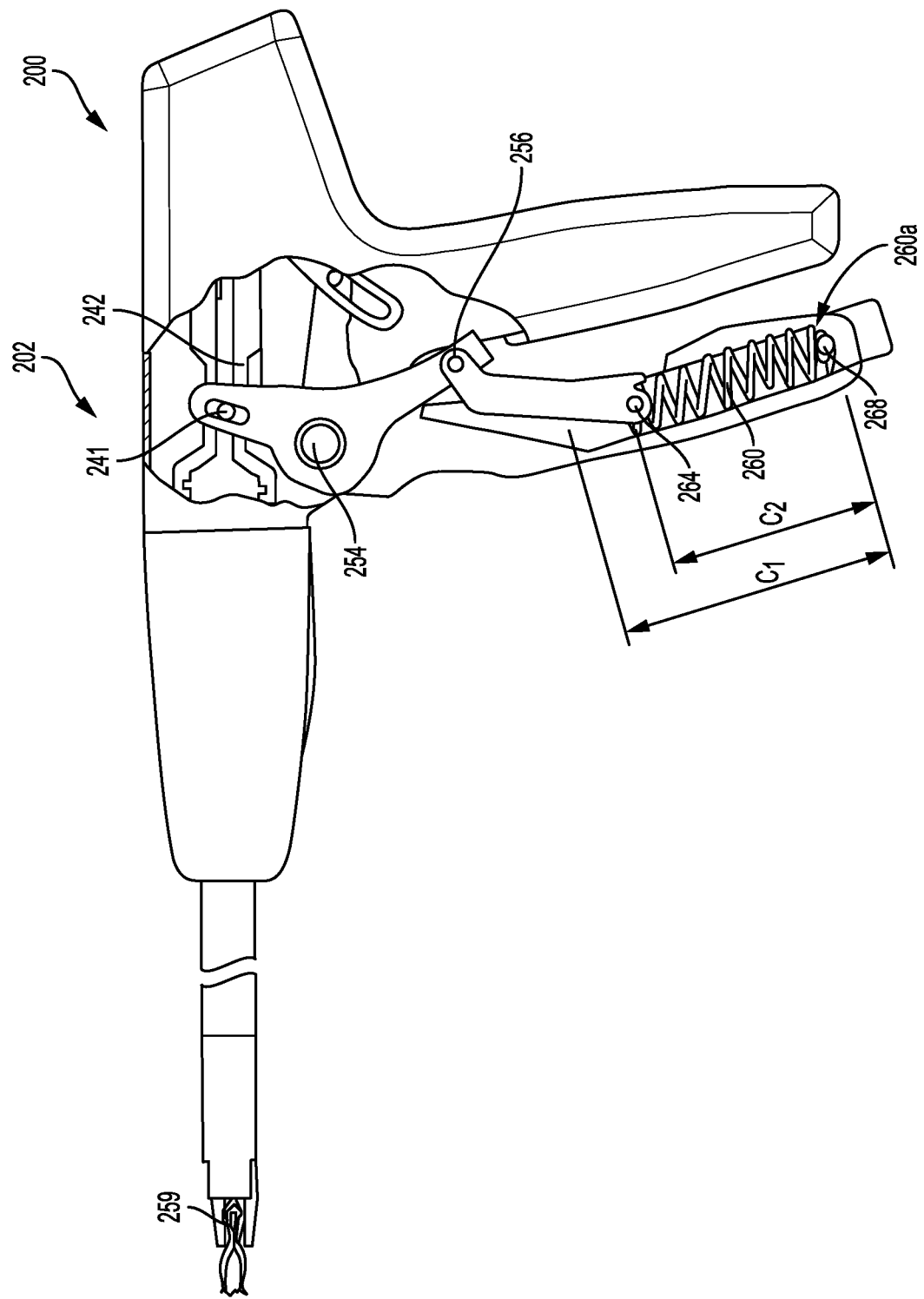
FIG. 5C is a perspective, partially transparent view of the surgical clip applier in FIG. 5A, showing the trigger in an actuated position and the overload member in a second position in which the biasing element is compressed.
Figure 6A:
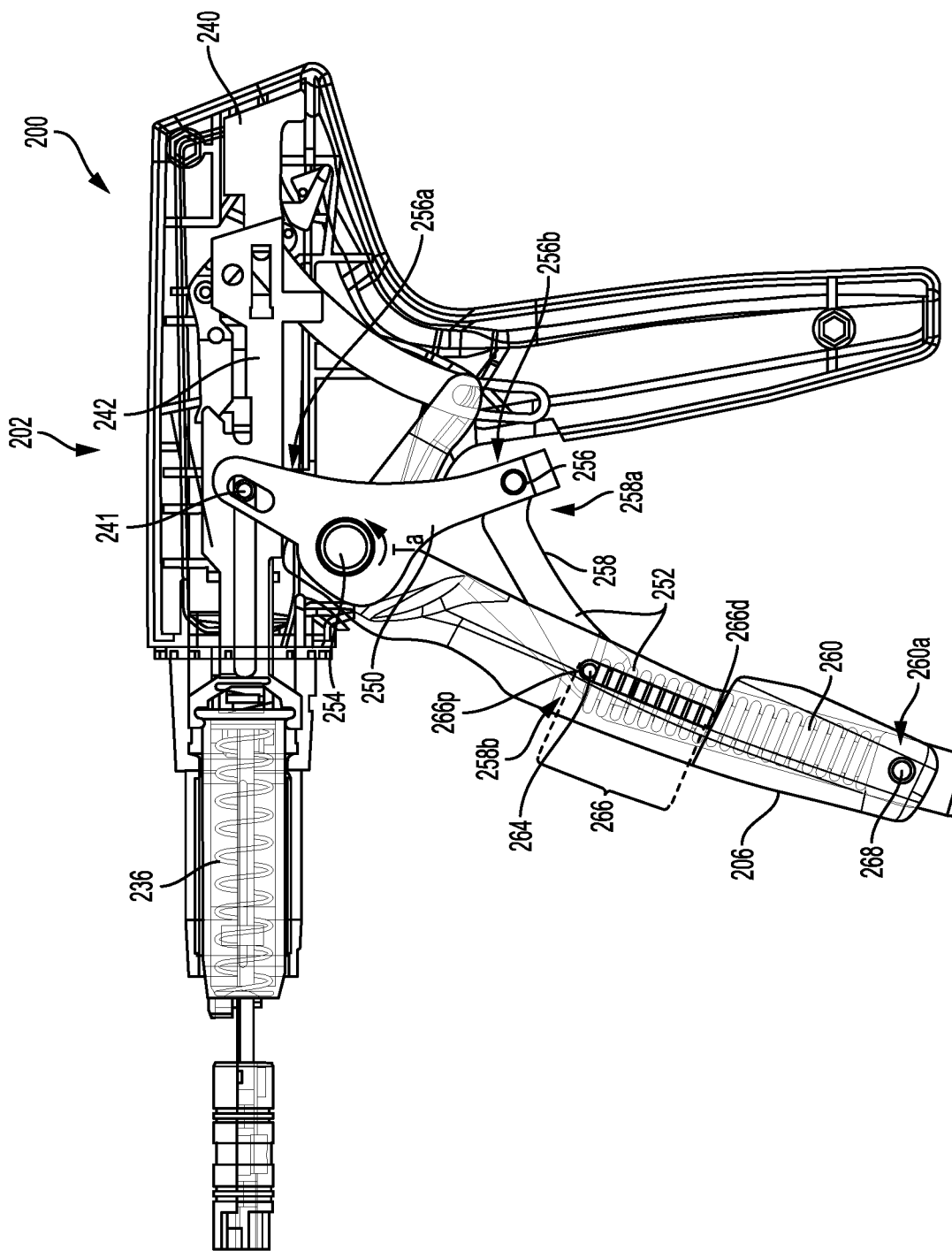
FIG. 6A is a perspective, partially transparent view of a proximal portion of the surgical clip applier in FIG. 5A.
Figure 6B:
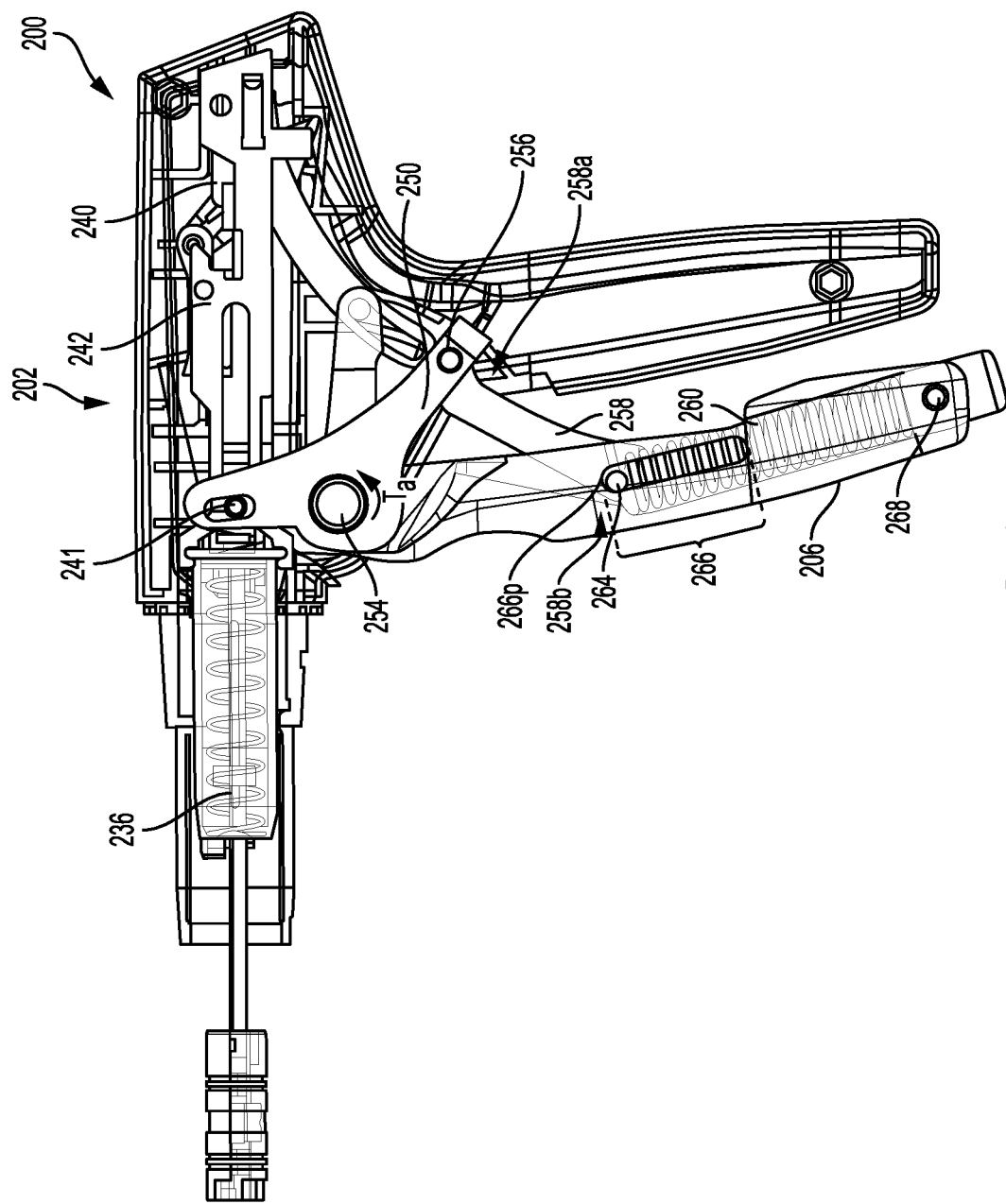
FIG. 6B is a perspective, partially transparent view of the proximal portion of the surgical clip applier in FIG. 5B.
Figure 6C:
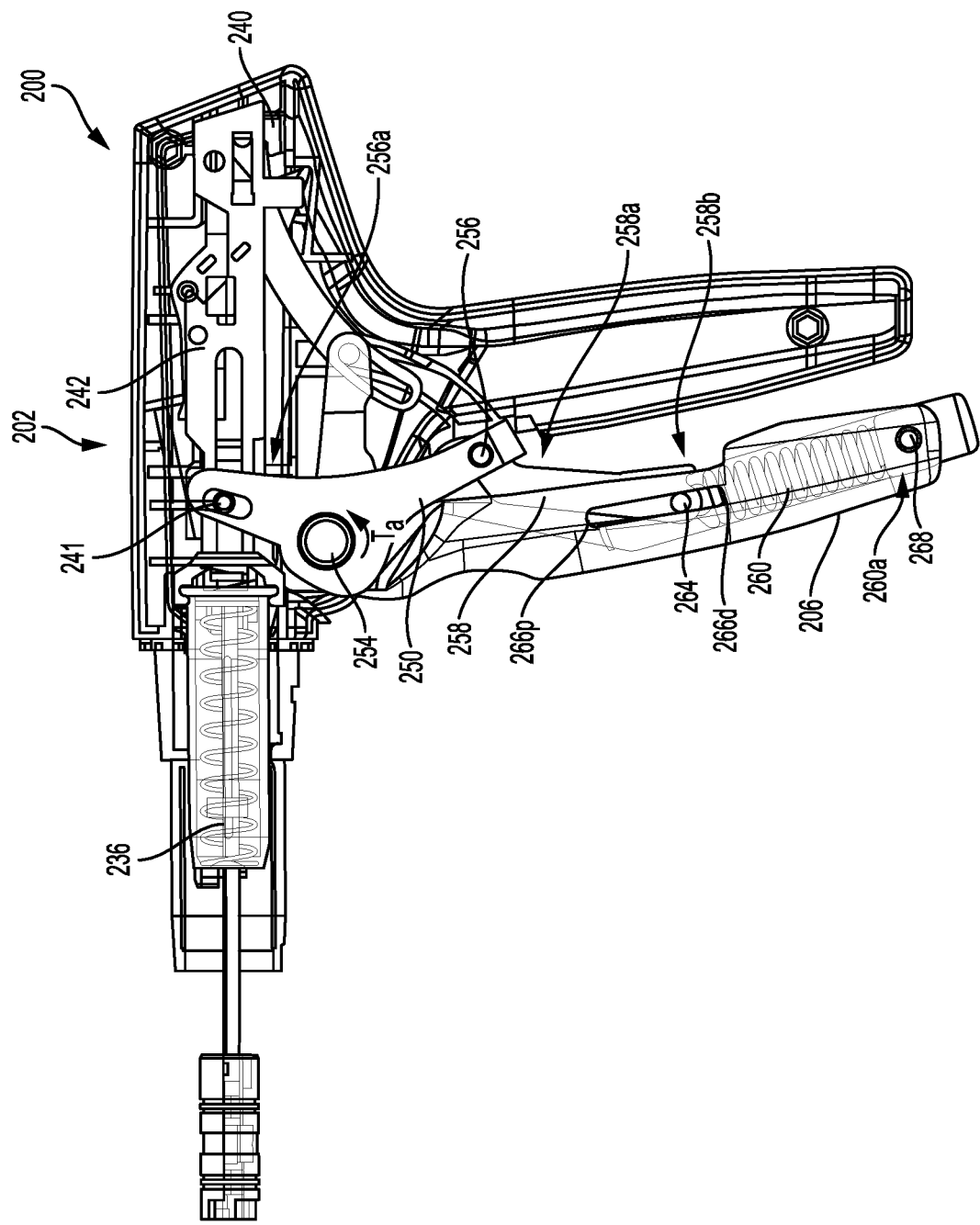
FIG. 6C is a perspective, partially transparent view of the proximal portion of the surgical clip applier in FIG. 5C.

FIGS. 5A-5C illustrate an exemplary embodiment of a surgical clip applier 200 that includes an overload mechanism. Similarly, FIG. 6A-6C illustrates proximal view of the surgical clip applier 200. Aside from the differences described in detail below, the surgical clip applier 200 can be similar to the surgical clip applier 100 (FIGS. 1-4B) and is therefore not described in detail herein. As shown, the overload mechanism includes a pivot linkage 250 and an overload member 252 that are coupled to one another and located between the trigger 206 and the clip forming assembly, specifically the former tube 236 and the former plate 240 of the clip forming assembly, resulting in an indirect coupling between the trigger 206 from the clip forming assembly. When the trigger 206 is actuated, it pivots about a trigger pin 254, which defines the trigger pivot axis ($T_a$), from an unactuated position (FIGS. 5A and 6A) to an actuated position (FIGS. 5B and 6B). This movement transfers a closing force from the trigger 206 through the overload member 252 to the pivot linkage 250, and consequently, to the clip forming assembly. Thus, unlike conventional surgical clip appliers, e.g., surgical clip applier 100 in FIGS. 1A-4B, the closing force is transferred from the trigger 206 to the overload member 252 and thereafter to the pivot linkage 250 such that the pivot linkage 250 engages the clip forming assembly and causes the clip forming assembly to distally advance and move the jaws 212, 214 from an open position to a closed position.

In general, the pivot linkage 250 can be coupled between the clip forming assembly and the overload member 252. As shown in FIGS. 5A-6C, the pivot linkage 250 can be somewhat V-shaped with a first end 256a coupled to the former plate 240 of the clip forming assembly via a dowel pin 241 and a second end 256b coupled to the overload member 252 at a pivot joint 256. During use of the surgical clip applier 200, the trigger 206 is actuated and pivots, along with the pivot linkage 250, about the trigger pin 254 to cause distal advancement of the clip forming assembly, as long as the force required to actuate the trigger 206 and close the jaws does not exceed the predetermined threshold force. The pivotal movement of the pivot linkage 250 will thus distally advance the former plate 240, and consequently the former tube 236, to cause the pair of jaws 212, 214 to move from the open position to the close position.

When an overload is encountered, for example, due to thick tissue, the former tube 236 and the former plate 242 of the clip forming assembly will exert a counter force (reaction force) against the first end 256a of the pivot linkage 250 which will prevent the pivot linkage 250 from moving to its distal-most position, thereby preventing the jaws from fully closing. At the same time, the trigger 206 is not yet at its actuated position. In order for the trigger 206 to reach its actuated position when an overload is encountered, an excessive closing force can be applied to the trigger 206. To avoid this excessive force from being transferred to the clip forming assembly, the pivot linkage 250 can remain stationary relative to the handle housing 202. That is, even though excessive force is being applied to the trigger 206 so as to arrive at its actuated position, no further pivotal movement of the pivot linkage 250 about the trigger pivot axis ($T_a$) occurs to distally advance the clip forming assembly. This is due to movement of the overload member 252, as described in detail below.

In general, the overload member 252 can be coupled between the second end 256b of the pivot linkage 250 and the trigger 206. While the overload member 252 can have a variety of configurations, the overload member 252 shown in FIGS. 5A-6C includes an overload linkage 258 and a biasing element 260. As shown in FIGS. 5A-6C, the overload linkage 258 has first and second ends 258a, 258b. The first end 258a is coupled to the second end 256b of the pivot linkage 250 at engagement pivot joint 256, and the second end 258b of the overload linkage 258 is slidably coupled to the trigger 206 via a movable pin 264. The movable pin 264 moves relative to the trigger 206 and can be housed in a slot 266 formed in the trigger 206. As shown in FIGS. 5A-6C, the slot 266 can extend completely through the wall of the trigger 206 such that movement of the movable pin 264 from a proximal end 266p to a distal end 266d of the slot 266 can be observed by a user. The overload linkage 258 is also operably connected to the biasing element 260, for example, a spring or other spring-like member, which is housed within the trigger 206.

While the biasing element 260 can have a variety of configuration, in one exemplary embodiment as shown in FIGS. 5A-6C, the biasing element 260 can be in the form of a helical spring that is housed within the trigger 206 and that has an end 260a that is coupled to the trigger 206 at an engagement point 268. The biasing element 260 can be initially precompressed to a first compressed state (CO to bias the overload linkage 258 to a first position when the trigger 206 pivots about the trigger pin 254, which defines the trigger pivot axis ($T_a$), from the unactuated to the actuated position until an overload is encountered. For example, as shown in FIGS. 5B and 6B, where no overload is encountered during the closing stroke of the trigger 206, the trigger 206 is in its fully actuated position and the biasing element 260 remains in the first compressed state (CO such that the movable pin 264 remains at the proximal end 266p of the slot 266. That is, the second end 258b of the overload linkage 258 has not yet slid distally within the trigger 206.

When the closing force exceeds the predetermined threshold force, the closing force can overcome the biasing force of the biasing element 260 to allow the overload linkage 258 to move from the first position to a second position, thereby preventing further movement of the pivot linkage 250 relative to the handle housing 202. For example, as shown in FIGS. 5C and 6C, when an overload is encountered during the closing stroke of the trigger 206 (e.g., due to an obstruction 259), the overload linkage 258 slides within the trigger 206 and compresses the biasing element 260 to a second compressed state ($C_2$). More specifically, when the closing force exceeds the predetermined threshold force, in order for the trigger 206 to reach its fully actuated position without causing further distal movement of the clip forming assembly, the overload linkage 258 transfers the excess closing force to the biasing element 260 by moving the movable pin 264 toward the distal end 266d of the slot 266 causing the biasing element 260 to compress. This allows the overload linkage 258 to move in a manner that prevents transfer of the closing force, when it exceeds the predetermined threshold force, to the pivot linkage 250 such that the pivot linkage 250, and consequently the clip forming assembly, can remain stationary. The predetermined threshold force can correspond to a force required to overcome the biasing force of the biasing element 260, and thus a biasing element 260 having a desired biasing force can be selected during manufacturing as required based on the particular configuration of the device and the forces required to close the jaws without causing damage to the jaws.

Figure 7B:
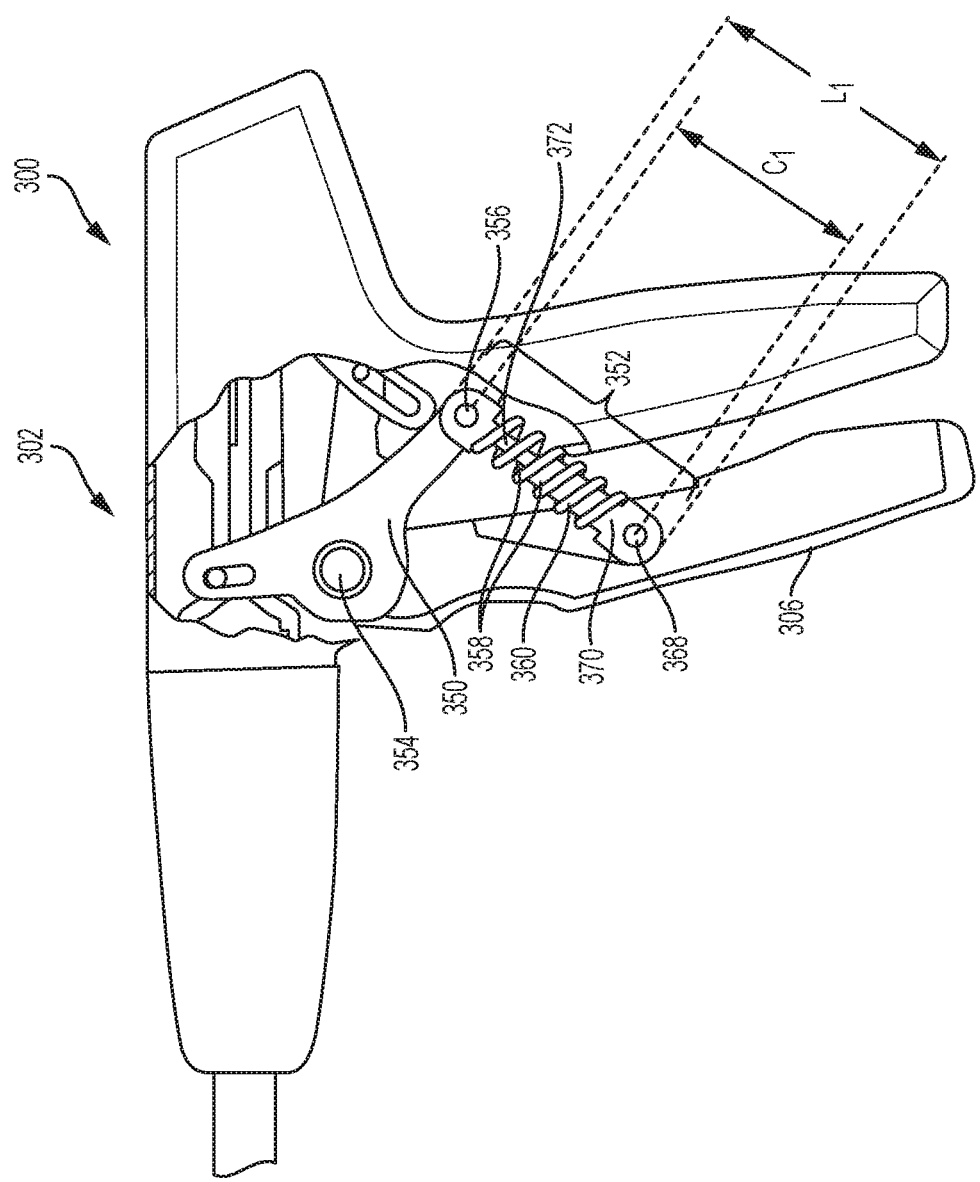
FIG. 7B is a perspective, partially transparent view of the proximal portion of the surgical clip applier in FIG. 7A, showing the trigger in an actuated position and the overload member in a first position without the biasing element being compressed.
Figure 7C:
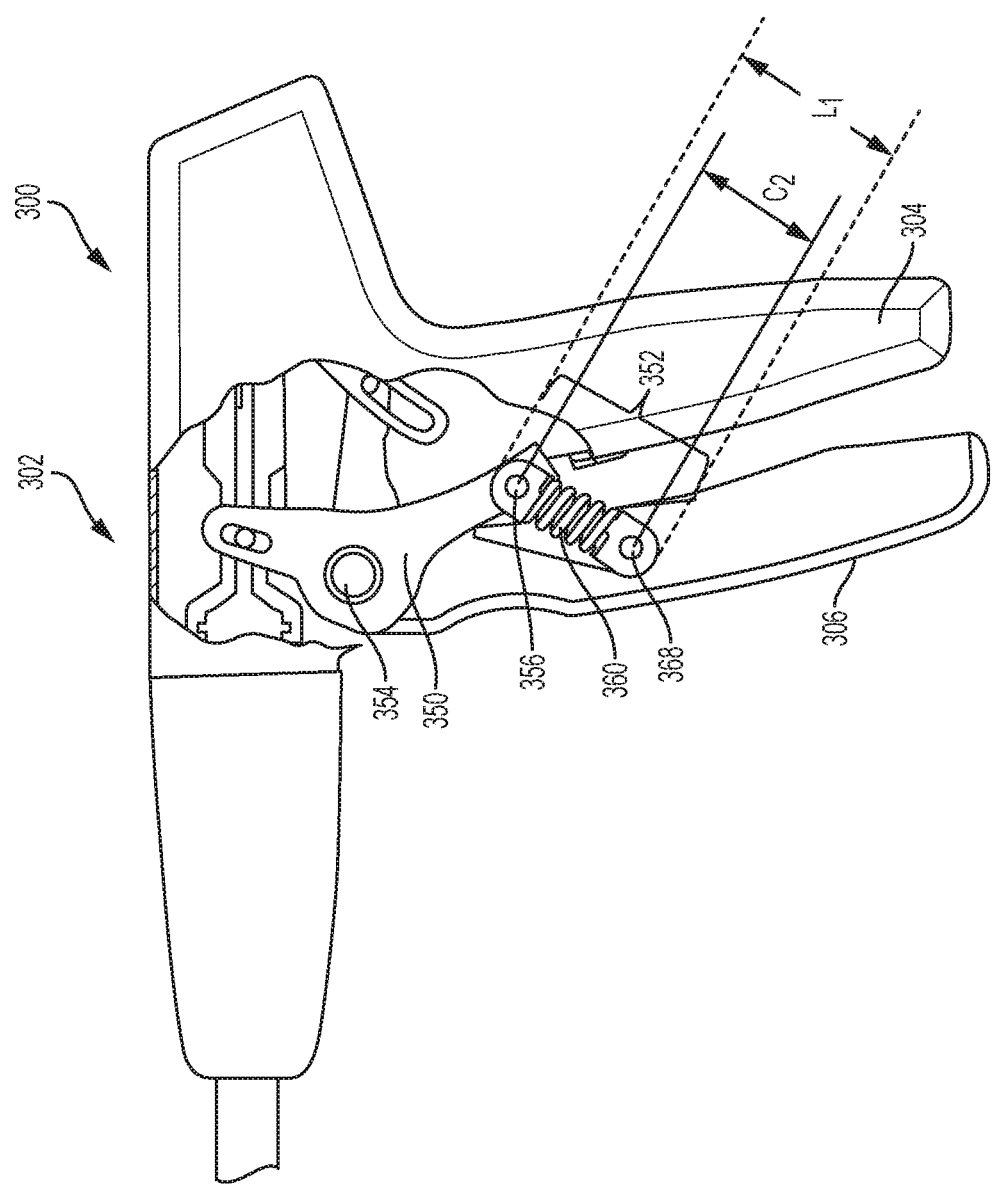
FIG. 7C is a perspective, partially transparent view of the proximal portion of the surgical clip applier in FIG. 7A, showing the trigger in an actuated position and the overload member in a second position in which the biasing element is compressed.

FIGS. 7A-7C illustrate another exemplary embodiment of an overload member disposed within a surgical clip applier 300 that is similar to surgical clip applier 100 (FIGS. 1-4B). As shown, the overload member 352 includes an overload linkage 358 having housing 370 that is coupled to the trigger 306 at an engagement point 368 and a pusher 372, e.g., a piston or piston-like member, that is coupled to the pivot linkage 350 at engagement point 356 and to the housing 370. As shown, the overload member 352 also includes a biasing element 360 that is positioned about the outer surface of the overload linkage 358. The biasing element 360 can bias the overload linkage 358 to a first position when the trigger 306 pivots about the trigger pin 354, which defines the trigger pivot axis ($T_a$), from the unactuated to the actuated position until an overload is encountered. For example, as shown in FIG. 7B, where no overload is encountered during the closing stroke of the trigger 306, the trigger 306 is in its fully actuated position and the biasing element 360 remains in an uncompressed state (C1). When the closing force exceeds the predetermined threshold force, the pusher 372 slides distally within the housing 370, thereby compressing the biasing element 360 to a compressed state (C2), thereby resulting in a decrease of the overall length of the overload member 352 from a first length ($L_1$) to a second length ($L_2$). The compression of the biasing element 360 prevents further movement of the pivot linkage 350 relative to the handle housing 302. Thus, the excessive closing force is transferred through the overload linkage 358 to the biasing element 360, rather than the clip forming assembly, thereby preventing the clip forming assembly from unduly forcing the jaws closed. As with the previous embodiment, the predetermined threshold force can correspond to the force required to overcome the biasing force of the biasing element 360, and may be selected as desired during manufacturing.

Figure 8:
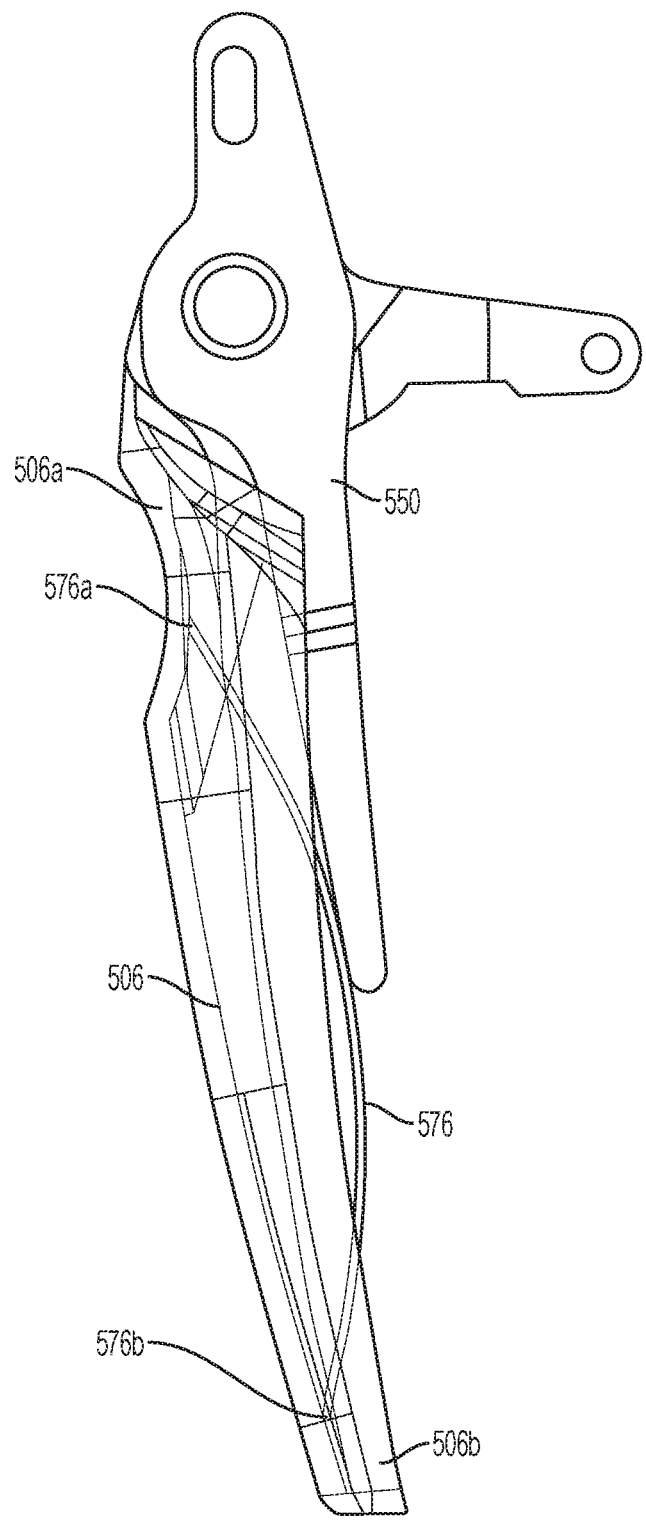
FIG. 8 is side, partially transparent view of another embodiment of a pivot linkage and an overload member operably coupled to one another, with the overload member including a biasing element coupled to a trigger.
Figure 9:
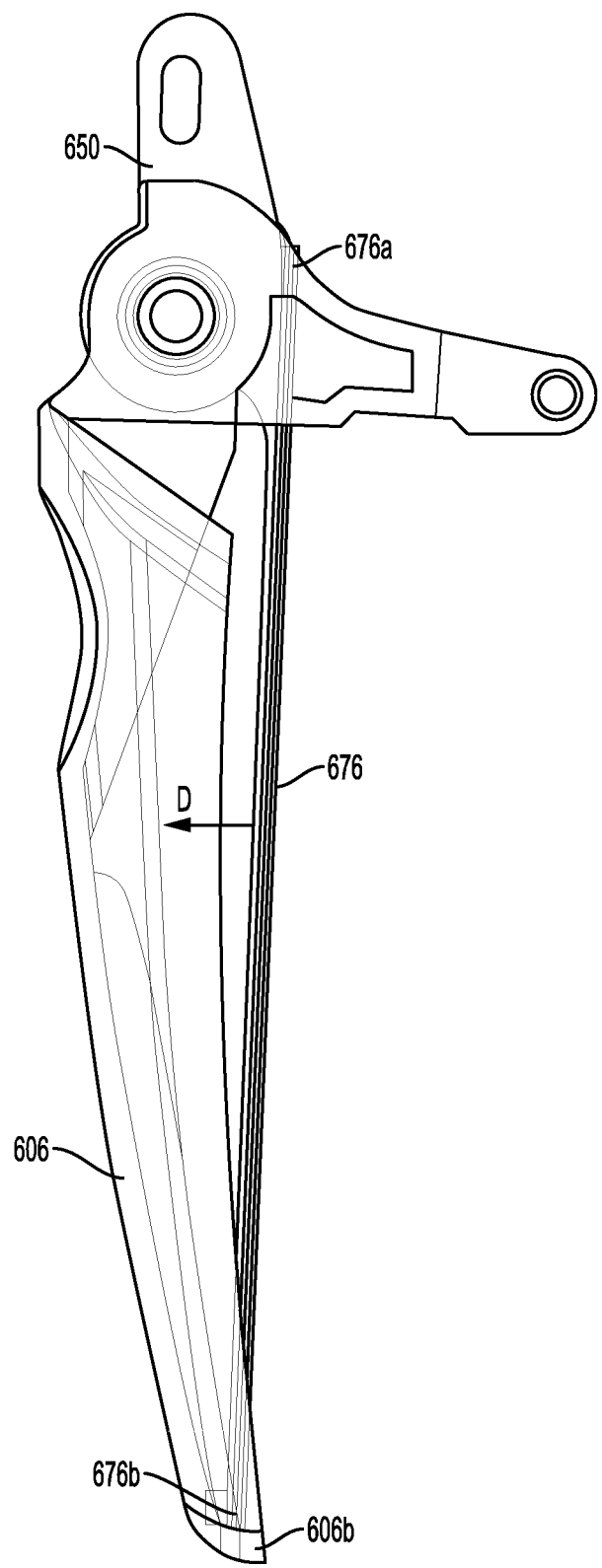
FIG. 9 is side, partially transparent view of a pivot linkage and an overload member having a biasing element coupled to the pivot linkage and a trigger, in accordance with another embodiment.
Figure 10:
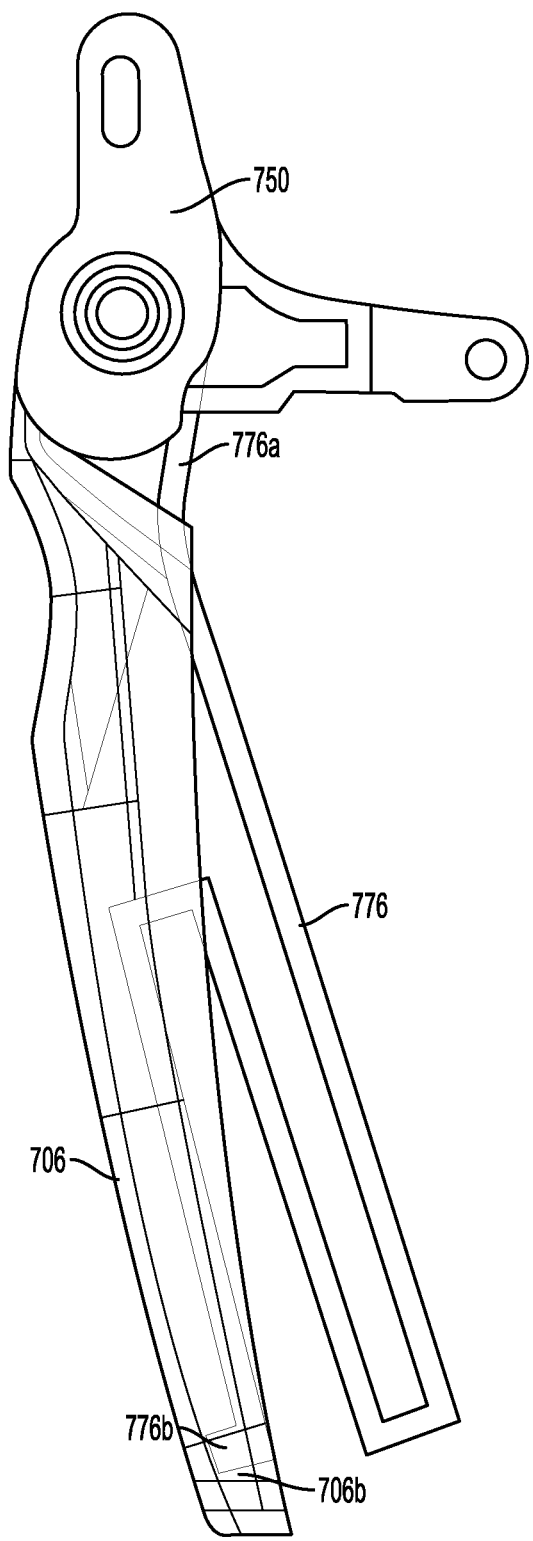
FIG. 10 is side, partially transparent view of another embodiment of a pivot linkage and an overload member that includes a biasing element coupled to the pivot linkage and a trigger.

While FIGS. 5A-7C illustrate overload members having an overload linkage 258, 358 and a biasing element 260, 360, in the form of a helical spring, the overload member can have other configurations, such as those shown in FIGS. 8-10. FIGS. 8-10 each illustrate an overload member that is in the form of a leaf spring 576, 676, 776. In FIG. 8, the leaf spring 576, which is illustrated as having an arc-shaped length, has a first end 576a coupled to a first end 506a of the trigger 506 and a second end 576b slidably disposed within the trigger adjacent to a second end 506b of the trigger 506. The arced mid-portion of the leaf spring 576 is in operable contact with the pivot linkage 550 such that the leaf spring 576 applies a biasing force to the pivot linkage 550. In use, when the closing force exceeds a predetermined threshold force, the continued movement of the trigger 506 to its actuated position transfers the closing force to the leaf spring 576. As a result, the leaf spring 576 compresses by flexing, causing its second end 576b to slide distally toward the second end 506b of the trigger 506, and thus, elongate and expand within the trigger 506, as shown. As such, no further movement of the pivot linkage 550 occurs relative to the handle housing.

In FIG. 9, the first end 676a of the leaf spring 676 is coupled to a pivot linkage 650 and a second end 676b is coupled to an end 606b of the trigger 606. The leaf spring 676 in this embodiment has a linear resting configuration in which a biasing force is applied to the pivot linkage 650. In use, when the closing force exceeds a predetermined threshold force, the continued movement of the trigger 606 to its actuated position transfers the closing force to the leaf spring 676 causing the leaf spring 676 to deform by bending in a direction (D) toward the trigger 606. In turn, the pivot linkage 650 can remain stationary relative to the handle housing.

Referring now to FIG. 10, the leaf spring 776 has a first end 776a coupled to the pivot linkage 750 and a second end 776b coupled to an end 706b of the trigger 706. The leaf spring 776 has two opposing U-shaped segments formed therein and biased to a spaced configuration in which a biasing force is applied to the pivot linkage 750. In use, when the closing force exceeds a predetermined threshold force, the continued movement of the trigger 706 to its actuated position transfers the closing force to the leaf spring 776. As a result, the leaf spring 776 compresses whereby the U-shaped segments collapse toward one another, so as to prevent further movement of the pivot linkage 750 relative to the handle housing.

Figure 11A:
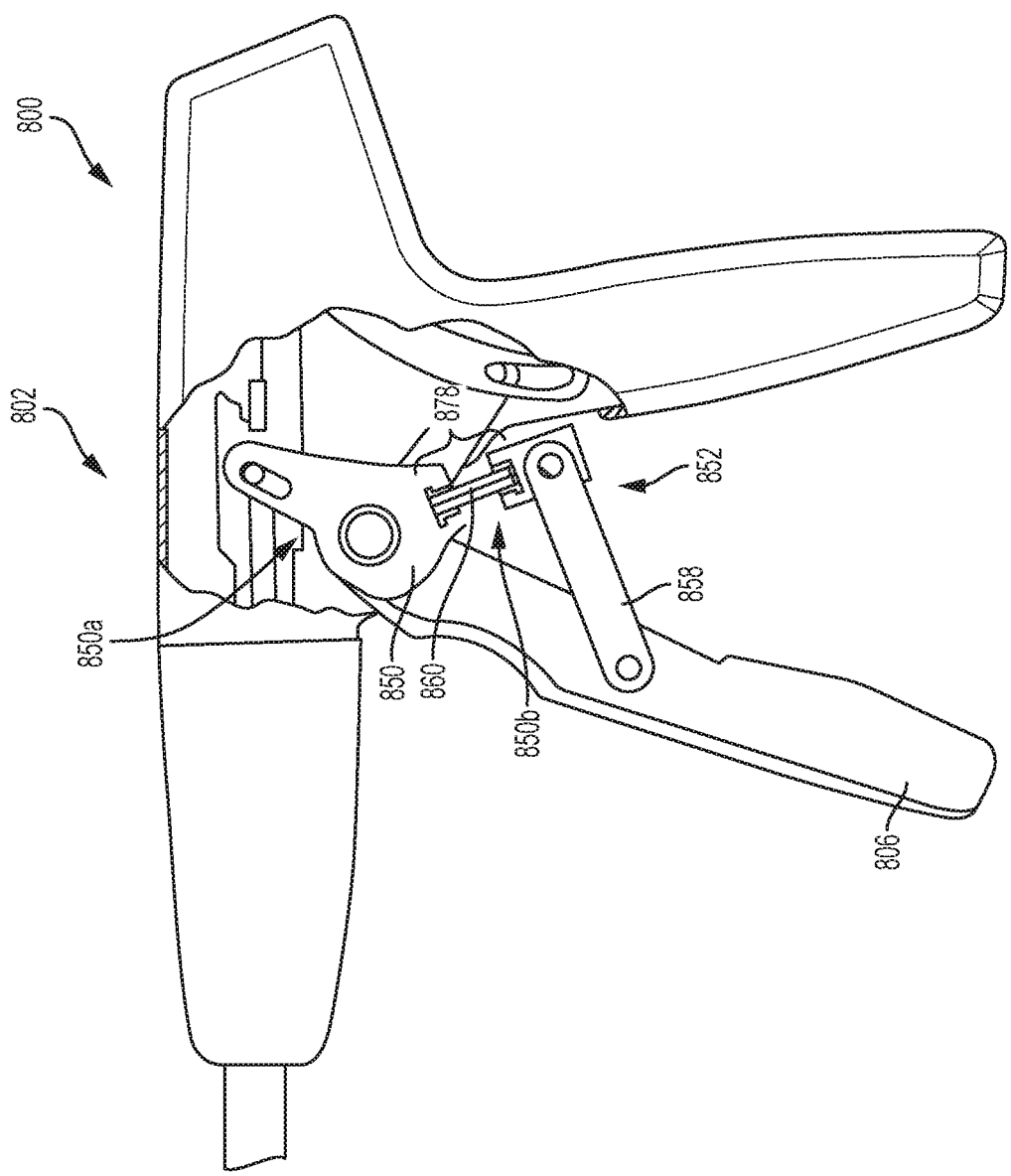
FIG. 11A is a perspective, partially transparent view of a proximal portion of another embodiment of a surgical clip applier that includes a pivot linkage and an overload member that includes an overload linkage and a biasing element that is a deflectable region of the pivot linkage, showing the trigger and the overload member in unactuated positions.
Figure 11B:
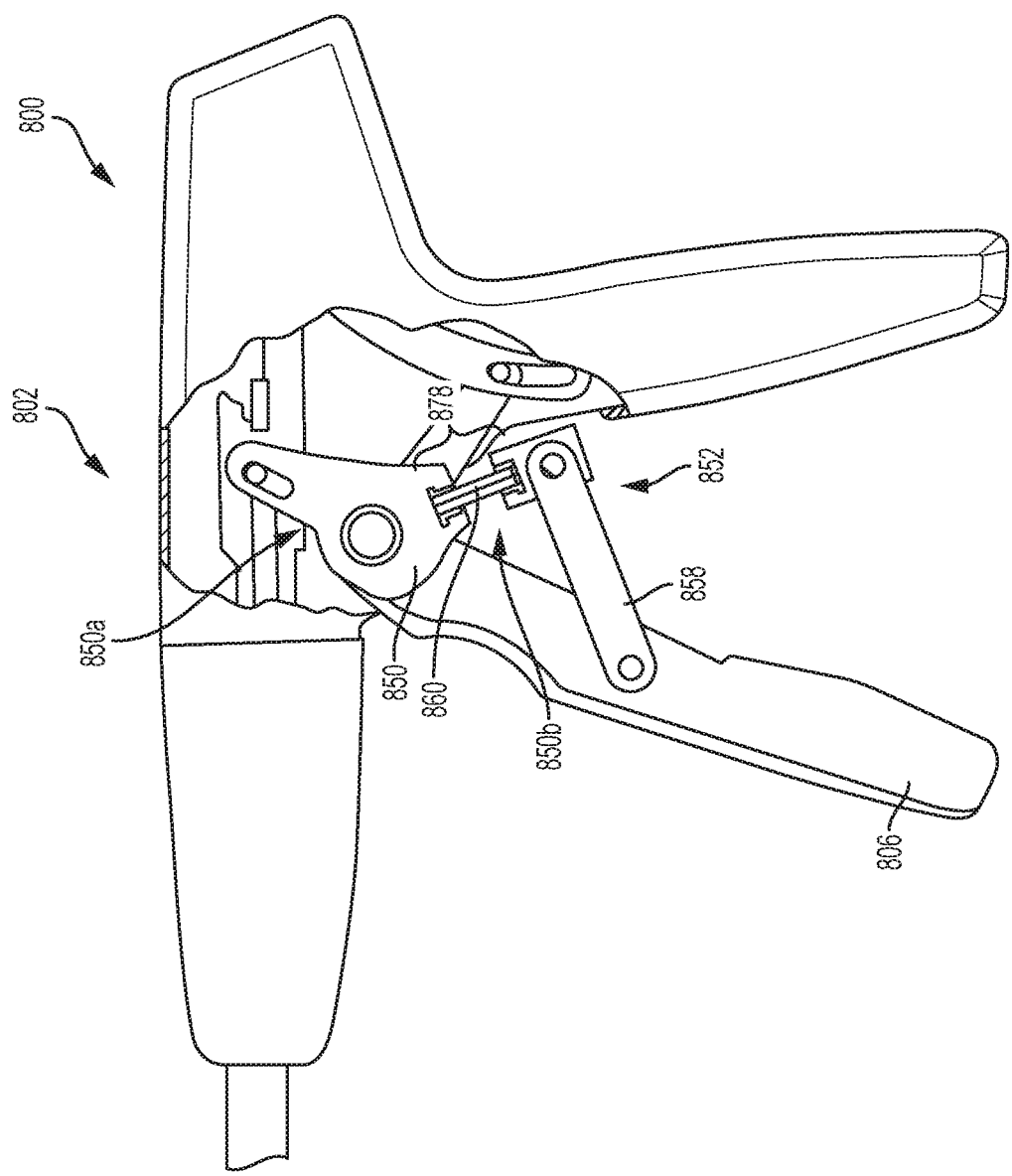
FIG. 11B is a perspective, partially transparent view of the proximal portion of the surgical clip applier in FIG. 11A, showing the trigger in an actuated position and the overload member in a first position without the biasing element being deformed.
Figure 11C:
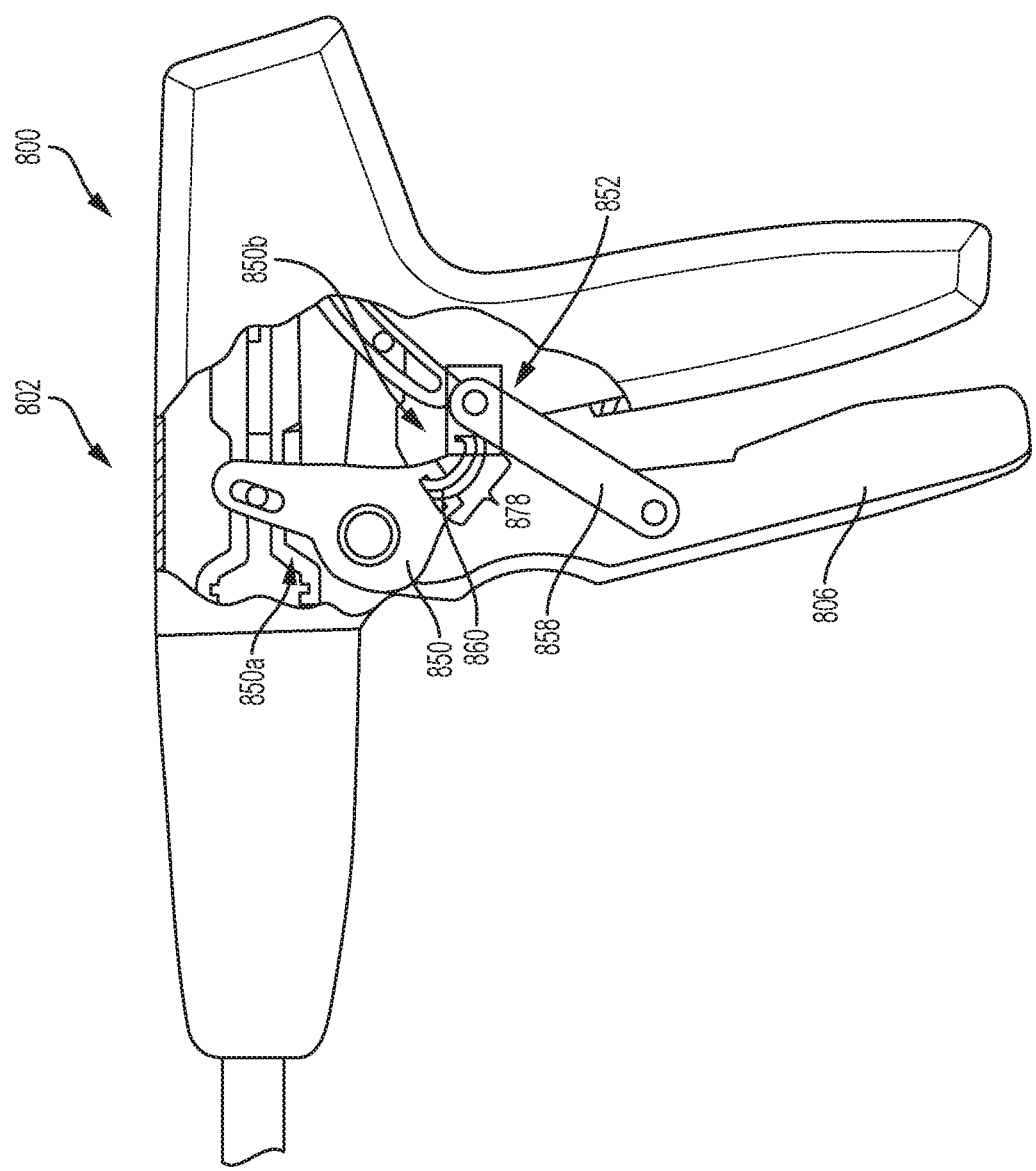
FIG. 11C is a perspective, partially transparent view of the proximal portion of the surgical clip applier in FIG. 11A, showing the trigger in an actuated position and the overload member in a second position in which the biasing element is deformed.

FIGS. 11A-11C illustrates another exemplary embodiment of an overload mechanism disposed within a surgical clip applier 800 that is similar to the surgical clip applier 100 (FIGS. 1-4B). As shown, the overload mechanism includes a pivot linkage 850 having first and second portions 850a, 850b and an overload member 852. The overload member 852 has an overload linkage 858 and a biasing element 860. In this embodiment, the biasing element 860 is a deflectable region 878 of the second portion 850b of the pivot linkage 850. As shown, for example, the biasing element can be a leaf spring. The biasing element 860 can bias the overload linkage 858 to a first position when the trigger 806 pivots about the trigger pivot axis from the unactuated to the actuated position until the closing force exceeds the predetermined threshold force. If no overload is encountered, the overload mechanism is not engaged, as illustrated in FIG. 11B. However, when an overload is encountered, as shown in FIG. 11C, the closing force overcomes the biasing force of the biasing element 860 to allow the overload member 852 to move to a second position so to prevent further movement of the pivot linkage 850 relative to the handle housing 802. More specifically, as shown in FIG. 11C, when the closing force exceeds the predetermined threshold force, the biasing element 860 deforms or deflects so that the first portion 850a of the pivot linkage 850, and thus the clip forming assembly, remain stationary while the trigger 806 continues to move to its actuated position.

The first portion 850a of the pivot linkage 850 can be less flexible than the second portion 850b of the pivot linkage 850. In one embodiment, the first portion is formed of a first material that has a first modulus of elasticity value and the second portion is formed of a second material that has a second modulus of elasticity that is less than the first modulus of elasticity value. In other embodiments, as shown in FIGS. 11A-11C, the second portion can be structured in a manner than allows the second portion to deflect or deform when excessive closing force is applied. In another embodiment, the second portion can have a narrower width than the first portion. In yet another embodiment, the second portion can have a non-solid cross section with either singular or repeating beam/rib elements, whereas the first portion can be solid or constructed of thicker beam/rib elements.

Figure 12B:
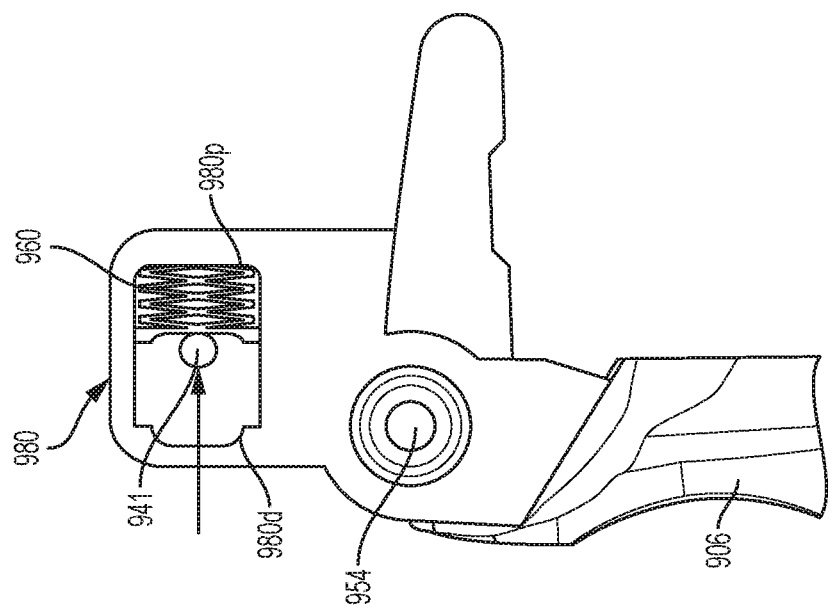
FIG. 12B is a perspective view of the overload mechanism in FIG. 12A when the closing force has exceeded the predetermined threshold force.
Figure 12A:
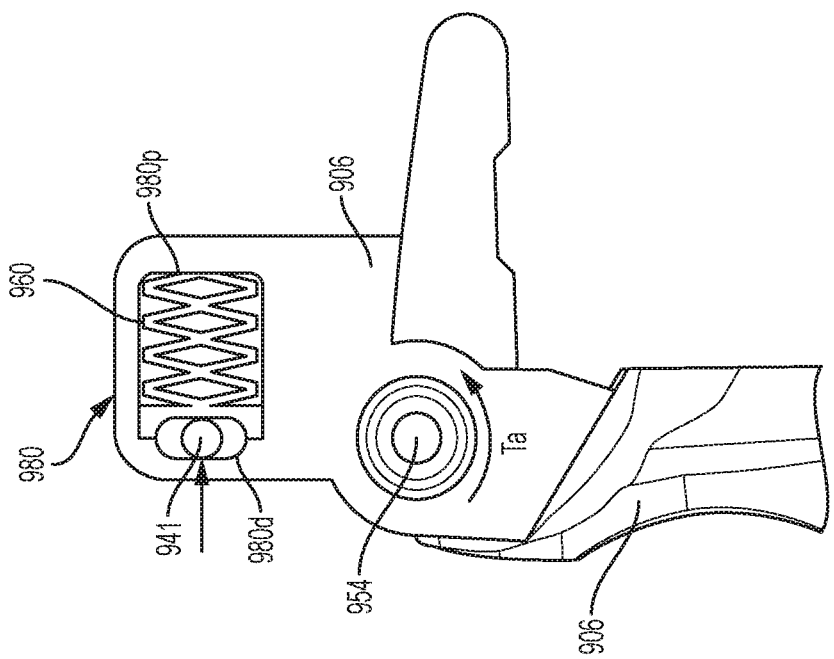
FIG. 12A is a perspective view of an embodiment of an overload mechanism when the closing force has not yet exceeded the predetermined threshold force.
Figure 13:
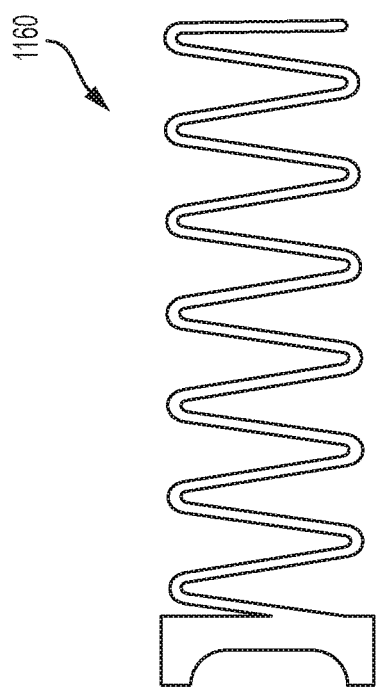
FIG. 13 is a side view of another embodiment of an overload mechanism when the closing force has not yet exceeded the predetermined threshold force.
Figure 14:
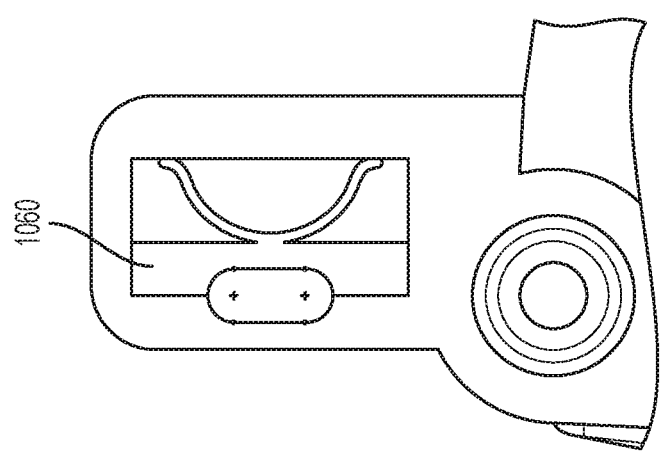
FIG. 14 is a side view of an embodiment of a biasing element.

FIGS. 12A-12B illustrates another exemplary embodiment of an overload mechanism. As shown, the overload mechanism includes a biasing element 960 disposed within a dowel pin slot 980 of the trigger 906. While the biasing element 960 can have a variety of configurations, the biasing in FIGS. 12A-12B is a spring in an accordion configuration. In other embodiments, for example, as illustrated in FIG. 13, the biasing element 1060 can be a leaf spring, or as shown in FIG. 14, the biasing element 1160 can be a planar spring in a zig-zag configuration.

Further, in FIGS. 12A-12B, a dowel pin 941, which connects the trigger 906 to the clip forming assembly, is also disposed within the dowel pin slot 980. The dowel pin 941 is located between a distal end 980d of the slot 980 and the biasing element 960 so that, during use, the dowel pin 941 is in operably contact with the biasing element 960. When the trigger 906 pivots about the trigger pin 954, which defines the trigger pivot axis ($T_a$), from the unactuated position to the actuated position, the biasing element 960 biases the dowel pin 941 against the distal end 980d of the slot 980 until the closing force exceeds the predetermined threshold force (FIG. 12A). If the closing force exceeds the predetermined threshold force during the trigger's closing stroke, the closing force overcomes the biasing force of the biasing element 960 causing the dowel pin 941 to move toward a proximal end 980p of the dowel pin slot 980, thereby compressing the biasing element 960 (FIG. 12B). As a result, the trigger 906 can continue to move to its actuated position without causing any further distal advancement of the clip forming assembly.

Figure 15B:
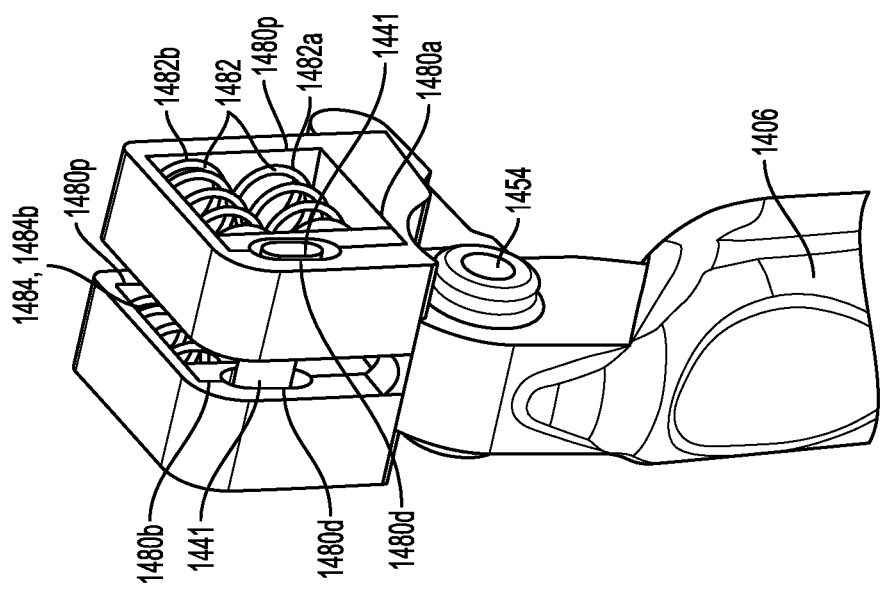
FIG. 15B is another perspective view of the overload mechanism in FIG. 15A.
Figure 15A:
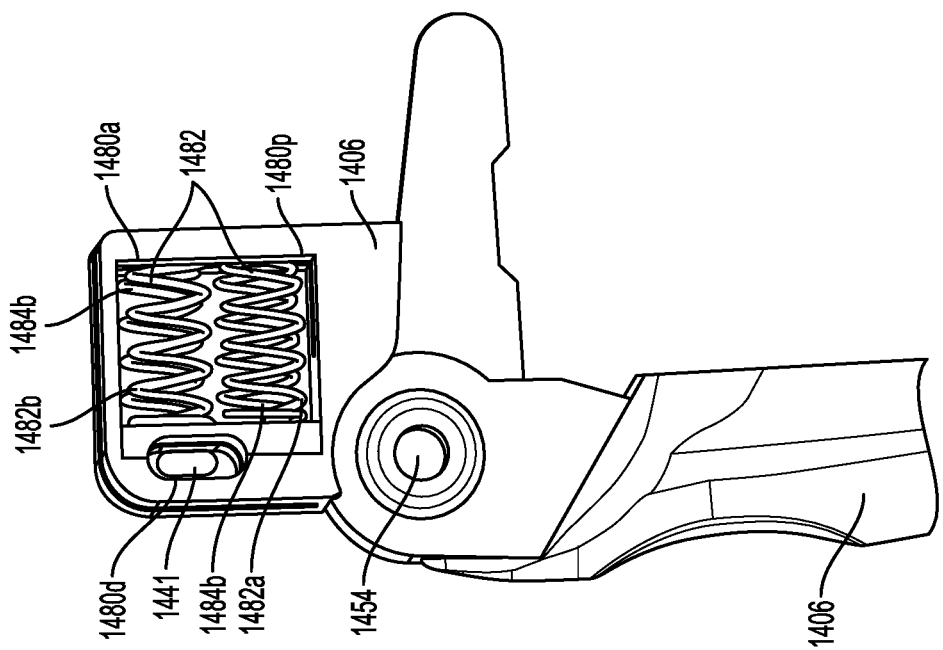
FIG. 15A is a perspective view of an overload mechanism when the closing force has not yet exceeded the predetermined threshold force according to another embodiment.

FIGS. 15A-15B illustrate another exemplary embodiment of an overload mechanism. As shown, the trigger 1406 includes two dowel pin slots 1480a, 1480b each having two biasing elements 1482, 1484. The first biasing element 1482 includes two coil springs 1482a, 1482b that are adjacent to one another. Similarly, the second biasing element 1484 includes two coil springs 1484a, 1484b that are adjacent to each other. A dowel pin 1441, which connects the trigger 1406 to the clip forming assembly, is also disposed within the dowel pin slots 1480a, 1480b. As shown, the dowel pin 1441 is located between the distal end 1480d of each slot 1480a 1480b and corresponding biasing element 1482, 1484 so that the dowel pin 1441 is operably connected to each biasing element 1482, 1484. In use, each biasing element 1482, 1484 biases the dowel pin 1441 against the distal end 1480d of each corresponding slot 1480 until the closing force exceeds the predetermined threshold force. During pivotal movement of the trigger 1406 about the trigger pin 1454 from the unactuated position to the actuated position, if the closing force exceeds the predetermined threshold force, the closing force is transferred to the overload mechanism, causing the dowel pin 1441 to move toward the proximal end 1480p of each dowel pin slot 1480a, 1480b, thereby compressing the corresponding biasing elements 1482, 1484. As discussed above, when an overload is encountered, the compression of the biasing elements 1482, 1484 allow the trigger 1406 to continue to move to its actuated position without causing any further distal advancement of the clip forming assembly.

As previously mentioned, surgical clip appliers can be used to form a clip about a surgical site, such as a vessel, duct, shunt, etc. Any suitable method can be used for operating any surgical device described herein. For example, when operating the surgical clip applier 200 (FIGS. 5A-5C), the pair of jaws, e.g., jaws 112, 114 shown in FIGS. 1-3, can be manipulated to position tissue therebetween. Once the jaws are positioned about the tissue, the trigger 206 (or other actuation device) of the surgical clip applier 200 can be actuated to transfer a force from the trigger 206 through the overload member 252 to the pivot linkage 250 to actuate the clip forming assembly, which in turn, moves the pair of jaws from an open position to a closed position. As a result, a clip, e.g., clip 127 shown in FIGS. 2-3, that is disposed within the jaws can be deformed such that the clip engages the tissue positioned between the jaws. In instances where the force exceeds a predetermined threshold force (i.e., a force corresponding to a force required to overcome the biasing force of the biasing element), the overload member 252 can move relative to the handle housing 202 to prevent the force from being transferred to at least a portion of the pivot linkage 250, and consequently the clip forming assembly. That is, if the force exceeds the predetermined threshold force, the overload member 252 can cause the pivot linkage 250 to remain stationary to thereby prevent further distal advancement of the clip forming assembly, and consequently, prevent the excessive closing force from causing undesirable damage to the tissue and/or the surgical device.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
a handle housing having an elongate shaft extending distally therefrom;
an end effector at the distal end of the elongate shaft;
a drive assembly configured to actuate the end effector;
a trigger coupled to the handle housing and pivotable about a trigger pivot axis from an unactuated position to an actuated position;
a pivot linkage having a first end coupled to a drive assembly and a second end, the pivot linkage being pivotable about the trigger pivot axis; and
an overload member coupled at least between the second end of the pivot linkage and the trigger, wherein the overload member includes an overload linkage and a biasing element that biases the overload linkage to a first position when the trigger pivots about the trigger pivot axis from the unactuated position to the actuated position until the closing force exceeds a predetermined threshold force, the overload linkage having a first end attached to the second end of the pivot linkage and a second end attached to the trigger;
wherein pivotal movement of the trigger about the trigger pivot axis from the unactuated position to the actuated position transfers a closing force through the overload member to the second end of the pivot linkage thereby causing the pivot linkage to pivot about the trigger pivot axis such that the first end of the pivot linkage distally advances the drive assembly to cause actuation of the end effector, and
wherein, when the closing force exceeds the predetermined threshold force, pivotal movement of the trigger about the trigger pivot axis from the unactuated position to the actuated position transfers the closing force to the overload member to compress the biasing element to cause at least one of deflection of the overload member and reduction of a length of the overload member to thereby prevent transfer of the closing force to the pivot linkage such that the pivot linkage remains stationary relative to the handle housing.

2. The device of claim 1, wherein, when the closing force exceeds the predetermined threshold force, the closing force overcomes a biasing force of the biasing element to allow the overload member to move from the first position to a second position, thereby preventing further movement of the pivot linkage relative to the handle housing.

3. The device of claim 1, wherein the second end of the overload linkage is slidably disposed within the trigger.

4. The device of claim 3, wherein the biasing element is housed within the trigger and, when the closing force exceeds the predetermined threshold force, the second end of the overload linkage slides within the trigger to compress the biasing element such that the pivotal linkage remains stationary relative to the handle housing.

5. The device of claim 1, wherein the biasing element is positioned about an outer surface of the overload linkage such that, when the closing force exceeds the predetermined threshold force, the biasing element compresses to prevent further movement of the pivot linkage relative to the handle housing.

6. The device of claim 5, wherein compression of the biasing element decreases a length of the overload member.

7. A surgical device, comprising:
a handle housing having a trigger pivotally coupled thereto;
an elongate shaft extending distally from the handle housing, the elongate shaft having an end effector at a distal end thereof;
a drive assembly that is movable to actuate the end effector;
a linkage assembly coupled between the trigger and the drive assembly, the linkage assembly including a pivot member and an overload shaft coupled to one another, the pivot member being coupled to the drive assembly and the overload shaft being coupled to the trigger, the linkage assembly being configured to transfer a driving force from the trigger, through the overload shaft to the pivot member to move the drive assembly and thereby actuate the end effector, and the linkage assembly being configured to cause the overload shaft to move while the pivot member remains stationary relative to the handle housing when the driving force exceeds a predetermined threshold force, wherein the pivot member includes first and second portions, wherein the overload shaft is operably connected to a biasing element that is a deflectable region of a distalthe second portion of the pivot member, and wherein the biasing element biases the overload shaft to a first position until the driving force exceeds the predetermined threshold force.

8. The device of claim 7, wherein, when the driving force exceeds the predetermined threshold force, the driving force causes the biasing element to move to allow the overload shaft to move from the first position to a second position, thereby preventing further movement of the pivot member relative to the handle housing.

9. The device of claim 7, wherein the biasing element is disposed within the trigger, the biasing element having first and second ends and the first end of the biasing element contacting an end of the overload shaft.

10. The device of claim 7, wherein the biasing element is positioned about an outer surface of the overload shaft.

11. The device of claim 7, wherein the first portion of the pivot member is less flexible than the second portion of the pivot member.

12. A surgical device, comprising:
a handle housing having an elongate shaft extending distally therefrom;
an end effector at the distal end of the elongate shaft;
a drive assembly configured to actuate the end effector;
a trigger coupled to the handle housing and pivotable about a trigger pivot axis from an unactuated position to an actuated position;
a pivot linkage having a first end coupled to a drive assembly and a second end, the pivot linkage being pivotable about the trigger pivot axis; and
an overload member coupled at least between the second end of the pivot linkage and the trigger, wherein the overload member includes an overload linkage having first and second ends in which the first end of the overload linkage is attached to the second end of the pivot linkage and the second end of the overload linkage is attached to and slidably disposed within the trigger;
wherein pivotal movement of the trigger about the trigger pivot axis from the unactuated position to the actuated position transfers a closing force through the overload member to the second end of the pivot linkage thereby causing the pivot linkage to pivot about the trigger pivot axis such that the first end of the pivot linkage distally advances the drive assembly to cause actuation of the end effector, and
wherein, when the closing force exceeds a predetermined threshold force, pivotal movement of the trigger about the trigger pivot axis from the unactuated position to the actuated position transfers the closing force to the overload member to cause the overload member to move in a manner that prevents transfer of the closing force to the pivot linkage such that the pivot linkage remains stationary relative to the handle housing.

13. The device of claim 12, wherein the overload member includes a biasing element, and wherein the biasing element biases the overload linkage to a first position when the trigger pivots about the trigger pivot axis from the unactuated position to the actuated position until the closing force exceeds the predetermined threshold force.

14. The device of claim 13, wherein the biasing element is housed within the trigger and, when the closing force exceeds the predetermined threshold force, the second end of the overload linkage slides within the trigger to compress the biasing element such that the pivotal linkage remains stationary relative to the handle housing.

15. The device of claim 13, wherein, when the closing force exceeds the predetermined threshold force, the closing force overcomes a biasing force of the biasing element to allow the overload member to move from the first position to a second position, thereby preventing further movement of the pivot linkage relative to the handle housing.

* * * * *